(12) United States Patent
Berinstein et al.

(10) Patent No.: US 8,021,664 B2
(45) Date of Patent: Sep. 20, 2011

(54) TUMOR ANTIGENS BFA5 FOR PREVENTION AND/OR TREATMENT OF CANCER

(75) Inventors: Neil Berinstein, Toronto (CA); Scott Gallichan, Campbellville (CA); Corey Lovitt, Bolton (CA); Mark Parrington, Bradford (CA); Artur Pedyczak, Pickering (CA); Laszlo Radvanyi, Houston, TX (US); Devender Singh-Sandhu, Thornhill (CA)

(73) Assignee: Sanofi Pasteur Limited, Toronto, Ontario (CA)

( * ) Notice: Subject to any disclaimer, the term of this patent is extended or adjusted under 35 U.S.C. 154(b) by 511 days.

(21) Appl. No.: 10/553,137
(22) PCT Filed: Apr. 15, 2004
(86) PCT No.: PCT/IB2004/001701
§ 371 (c)(1), (2), (4) Date: Feb. 25, 2008
(87) PCT Pub. No.: WO2004/092212
PCT Pub. Date: Oct. 28, 2004

(65) Prior Publication Data
US 2008/0138365 A1 Jun. 12, 2008

Related U.S. Application Data

(60) Provisional application No. 60/462,945, filed on Apr. 15, 2003.

(51) Int. Cl.
A61K 38/08 (2006.01)
A61K 39/00 (2006.01)
C07K 7/06 (2006.01)

(52) U.S. Cl. ............ 424/184.1; 424/277.1; 514/19.4; 514/21.6; 530/328

(58) Field of Classification Search .................. None
See application file for complete search history.

(56) References Cited

U.S. PATENT DOCUMENTS

| | | | |
|---|---|---|---|
| 6,911,529 B1 * | 6/2005 | Jager et al. ............. | 530/350 |
| 6,969,518 B2 | 11/2005 | Houghton et al. | |
| 2004/0223949 A1 | 11/2004 | Astsaturov et al. | |
| 2005/0112099 A1 * | 5/2005 | Berinstein et al. ........... | 424/93.2 |
| 2006/0154291 A1 * | 7/2006 | Billing-Medel et al. ......... | 435/6 |
| 2007/0128655 A1 | 6/2007 | Obata | |

FOREIGN PATENT DOCUMENTS

| | | | |
|---|---|---|---|
| WO | WO 01/47959 A * | 7/2001 | |
| WO | WO0147959 A2 | 7/2001 | |
| WO | WO 2004/037284 A * | 5/2004 | |
| WO | WO2004092212 A3 | 10/2004 | |
| WO | WO 2004104039 A2 * | 12/2004 | |

OTHER PUBLICATIONS

Jaeger et al. Identification of tumor-restricted antigens . . . Cancer Immunity. Jun. 28, 2002, vol. 2, p. 5.*
Jager et al. Identification of a tissue-specific putative transcription factor . . . Cancer Research. Mar. 1, 2001, vol. 61, No. 5, pp. 2055-2061.*
Jager, et al. Identification of a naturally processed NY-ESO-1 peptide recognized by CD8+ T cells in the context of HLA-B51. Cancer Immunity, vol. 2, p. 12 (2002).
Jager, et al. Identification of a Tissue-specific Putative Transcription Factor in Breast Tissue by Serological Screening of a Cancer Library. Cancer Research, 61: 2055-2061 (2001).

Sharma, et al. Class I Major Histocompatibility Complex Anchor Substitutions Alter the Conformation of T Cell Receptor Contacts. J. Biol. Chem. 276(24): 21443-21449 (2001).

* cited by examiner

Primary Examiner — Jeffrey E Russel
(74) Attorney, Agent, or Firm — Patrick J. Halloran; Reza Yacoob

(57) ABSTRACT

The present invention relates to a nucleic acid encoding a polypeptide and the use of the nucleic acid or polypeptide in preventing and/or treating cancer. In particular, the invention relates to improved vectors for the insertion and expression of foreign genes encoding tumor antigens for use in immunotherapeutic treatment of cancer.

MTKRKKTINLNIQDAQKRTALHWACVNGHEEVVTFLVDRKCQLDVLDG

EHRTPLMKALQCHQEACANILIDSGADINLVDVYGNMALHYAVYSEIL

SVVAKLLSHGAVIEVHNKASLTPLLLSITKRSEQIVEFLLIKNANANA

VNKYKCTALMLAVCHGSSEIVGMLLQQNVDVFAADICGVTAEHYAVTC

GFHHIHEQIMEYIRKLSKNHQNTNPEGTSAGTPDEAAPLAERTPDTAE

SLVEKTPDEAAPLVERTPDTAESLVEKTPDEAASLVEGTSDKIQCLEK

ATSGKFEQSAEETPREITSPAKETSEKFTWPAKGRPRKIAWEKKEDTP

REIMSPAKETSEKFTWAAKGRPRKIAWEKKETFVKTGCVARVTSNKTK

VLEKGRSKMIACPTKESSTKASANDQRFPSESKQEEDEEYSCDSRSLF

ESSAKIQVCIPESIYQKVMEINREVEEPPKKPSAFKPAIEMQNSVPNK

AFELKNEQTLRADPMFPPESKQKDYEENSWDSESLCETVSQKDVCLPK

ATHQKEIDKINGKLEESPNKDGLLKATCGMKVSIPTKALELKDMQTFK

AEPPGKPSAFEPATEMQKSVPNKALELKNEQTWRADEILPSESKQKDY

EENSWDTESLCETVSQKDVCLPKAAHQKEIDKINGKLEGSPVKDGLLK

ANCGMKVSIPTKALELMDMQTFKAEPPEKPSAFEPAIEMQKSVFNKAL

ELKNEQTLRADEILPSESKQKDYEESSWDSESLCETVSQKDVCLPKAT

HQKEIDKINGKLEESPDNDGFLKAPCRMKVSIPTKALELMDMQTFKAE

PPEKPSAFEPAIEMQKSVPNKALELKNEQTLRADQMFPSESKQKKVEE

NSWDSESLRETVSQKDVCVPKATHQKEMDKISGKLEDSTSLSKILDTV

HSCERARELQKDHCEQRTGKMEQMKKKFCVLKKKLSEAKEIKSQLENQ

KVKWEQELCSVRLTLNQEEEKRRNADILNEKIREELGRIEEQERKELE

VKQQLEQALRIQDIELKSVESNLNQVSHTHENENYLLHENCMLKKEIA

MLKLEIATLKHQYQEKENKYFEDIKILKEKNAELQMTLKLKEESLTKR

ASQYSGQLKVLIAENTMLTSKLKEKQDKEILEAEIESHHPRLASAVQD

HDQIVTSRKSQEPAFHIAGDACLQRKMNVDVSSTIYNNEVLHQPLSEA

QRKSKSLKINLNYAGDALRENTLVSEHAQRDQRETQCQMKEAEHMYQN

EQDNVNKHTEQQESLDQKLFQLQSKNMWLQQQLVHAHLLADNKSKITI

DIHFLERKMQHHLLKEKNEEIFNYNNHLKNRIYQYEKEKAETENS

8 Claims, 5 Drawing Sheets

FIGURE 1

*BFA4 cDNA Sequence*

```
ATGGTCCGGAAAAAGAACCCCCCTCTGAGAAACGTTGCAAGTGAAGGCGAGGGCCAGATCCTGGAGCCTATAGGTACAGAAAGCAA
GGTATCTGGAAAGAACAAAGAATTCTCTGCAGATCAGATGTCAGAAAATACGGATCAGAGTGATGCTGCAGAACTAAATCATAAGGA
GGAACATAGCTTGCATGTTCAAGATCCATCTTCTAGCAGTAAGAAGGACTTGAAAAGCGCAGTTCTGAGTGAGAAGGCTGGCTTCAA
TTATGAAAGCCCCAGTAAGGGAGGAAACTTTCCCTCCTTTCCGCATGATGAGGTGACAGACAGAAATATGTTGGCTTTCTCATTTCC
AGCTGCTGGGGGAGTCTGTGAGCCCTTGAAGTCTCCGCAAAGAGCAGAGGCAGATGACCCTCAAGATATGGCCTGCACCCCCTCAGG
GGACTCACTGGAGACAAAGGAAGATCAGAAGATGTCACCAAAGGCTACAGAGGAAACAGGGCAAGCACAGAGTGGTCAAGCCAATTG
TCAAGGTTTGAGCCCAGTTTCAGTGGCCTCAAAAAACCCACAAGTGCCTTCAGATGGGGGTGTAAGACTGAATAAATCCAAAACTGA
CTTACTGGTGAATGACAACCCAGACCCGGCACCTCTGTCTCCAGAGCTTCAGGACTTTAAATGCAATATCTGTGGATATGGTTACTA
CGGCAACGACCCCACAGATCTGATTAAGCACTTCCGAAAGTATCACTTAGGACTGCATAACCGCACCAGGCAAGATGCTGAGCTGGA
CAGCAAAATCTTGGCCCTTCATAACATGGTGCAGTTCAGCCATTCCAAAGACTTCCAGAAGGTCAACCGTTCTGTGTTTTCTGGTGT
GCTGCAGGACATCAATTCTTCAAGGCCTGTTTTACTAAATGGGACCTATGATGTGCAGGTGACTTCAGGTGGAACATTCATTGGCAT
TGGACGGAAAACACCAGATTGCCAAGGGAACACCAAGTATTTCCGCTGTAAATTCTGCAATTTCACTTATATGGGCAACTCATCCAC
CGAATTAGAACAACATTTTCTTCAGACTCACCCAAACAAAATAAAAGCTTCTCTCCCCTCCTCTGAGGTTGCAAAACCTTCAGAGAA
AAACTCTAACAAGTCCATCCCTGCACTTCAATCCAGTGATTCTGGAGACTTGGGAAAATGGCAGGACAAGATAACAGTCAAAGCAGG
AGATGACACTCCTGTTGGGTACTCAGTGCCCATAAAGCCCCTCGATTCCTCTAGACAAAATGGTACAGAGGCCACCAGTTACTACTG
GTGTAAATTTTGTAGTTTCAGCTGTGAGTCATCTAGCTCACTTAAACTGCTAGAACATTATGGCAAGCAGCACGGAGCAGTGCAGTC
AGGCGGCCTTAATCCAGAGTTAAATGATAAGCTTTCCAGGGGCTCTGTCATTAATCAGAATGATCTAGCCAAAAGTTCAGAAGGAGA
GACAATGACCAAGACAGACAAGAGCTCGAGTGGGGCTAAAAAGAAGGACTTCTCCAGCAAGGGAGCCGAGGATAATATGGTAACGAG
CTATAATTGTCAGTTCTGTGACTTCCGATATTCCAAAAGCCATGGCCCTGATGTAATTGTAGTGGGCCACTTCTCCGTCATTATCA
ACAGCTCCATAACATTCACAAGTGTACCATTAAACACTGTCCATTCTGTCCCAGAGGACTTTGCAGCCCAGAAAAGCACCTTGGAGA
AATTACTTATCCGTTTGCTTGTAGAAAAAGTAATTGTTCCCACTGTGCACTCTTGCTTCTGCACTTGTCTCCTGGGGCGGCTGGAAG
CTCGCGAGTCAAACATCAGTGCCATCAGTGTTCATTCACCACCCCTGACGTAGATGTACTCCTCTTTCACTATGAAAGTGTGCATGA
GTCCCAAGCATCGGATGTCAAACAAGAAGCAAATCACCTGCAAGGATCGGATGGGCAGCAGTCTGTCAAGGAAAGCAAAGAACACTC
ATGTACCAAATGTGATTTTATTACCCAAGTGGAAGAAGAGATTTCCCGACACTACAGGAGAGCACACAGCTGCTACAAATGCCGTCA
GTGCAGTTTTACAGCTGCCGATACTCAGTCACTACTGGAGCACTTCAACACTGTTCACTGCCAGGAACAGGACATCACTACAGCCAA
CGGCGAAGAGGACGGTCATGCCATATCCACCATCAAAGAGGAGCCCAAAATTGACTTCAGGGTCTACAATCTGCTAACTCCAGACTC
TAAAATGGGAGAGCCAGTTTCTGAGAGTGTGGTGAAGAGAGAGAAGCTGGAAGAGAAGGACGGGCTCAAAGAGAAAGTTTGGACCGA
GAGTTCCAGTGATGACCTTCGCAATGTGACTTGGAGAGGGGCAGACATCCTGCGGGGGAGTCCGTCATACACCCAAGCAAGCCTGGG
GCTGCTGACGCCTGTGTCTGGCACCCAAGAGCAGACAAAGACTCTAAGGGATAGTCCCAATGTGGAGGCCGCCCATCTGGCGCGACC
TATTTATGGCTTGGCTGTGGAAACCAAGGGATTCCTGCAGGGGCGCCAGCTGGCGGAGAGAAGTCTGGGGCCCTCCCCCAGCAGTA
TCCTGCATCGGAGAAAACAAGTCCAAGGATGAATCCCAGTCCCTGTTACGGAGGCGTAGAGGCTCCGGTGTTTTTTGTGCCAATTG
CCTGACCACAAAGACCTCTCTCTGGCGAAAGAATGCAAATGGCGGATATGTATGCAACGCGTGTGGCCTCTACCAGAAGCTTCACTC
GACTCCCAGGCCTTTAAACATCATTAAACAAAACAACGGTGAGCAGATTATTAGGAGGAGAACAAGAAAGCGCCTTAACCCAGAGGC
ACTTCAGGCTGAGCAGCTCAACAAACAGCAGAGGGGCAGCAATGAGGAGCAAGTCAATGGAAGCCCGTTAGAGAGGAGGTCAGAAGA
TCATCTAACTGAAAGTCACCAGAGAGAAATTCCACTCCCCAGCCTAAGTAAATACGAAGCCCAGGGTTCATTGACTAAAAGCCATTC
TGCTCAGCAGCCAGTCCTGGTCAGCCAAACTCTGGATATTCACAAAAGGATGCAACCTTTGCACATTCAGATAAAAAGTCCTCAGGA
AAGTACTGGAGATCCAGGAAATAGTTCATCCGTATCTGAAGGGAAAGGAAGTTCTGAGAGAGGCAGTCCTATAGAAAAGTACATGAG
ACCTGCGAAACACCCAAATTATTCACCACCAGGCAGCCCTATTGAAAAGTACCAGTACCCACTTTTTGGACTTCCCTTTGTACATAA
TGACTTCCAGAGTGAAGCTGATTGGCTGCGGTTCTGGAGTAAATATAAGCTCTCCGTTCCTGGGAATCCGCACTACTTGAGTCACGT
GCCTGGCCTACCAAATCCTTGCCAAAACTATGTGCCTTATCCCACCTTCAATCTGCCTCCTCATTTTTCAGCTGTTGGATCAGACAA
TGACATTCCTCTAGATTTGGCGATCAAGCATTCCAGACCTGGGCCAACTGCAAACGGTGCCTCCAAGGAGAAAACGAAGGCACCACC
AAATGTAAAAAATGAAGGTCCCTTGAATGTAGTAAAAACAGAGAAAGTTGATAGAAGTACTCAAGATGAACTTTCAACAAAATGTGT
GCACTGTGGCATTGTCTTTCTGGATGAAGTGATGTATGCTTTGCATATGAGTTGCCATGGTGACAGTGGACCTTTCCAGTGCAGCAT
ATGCCAGCATCTTTGCACGGACAAATATGACTTCACAACACATATCCAGAGGGGCCTGCATAGGAACAATGCACAAGTGGAAAAAAA
TGGAAAACCTAAAGAGTAA*
```

FIGURE 2

*BFA4 Amino Acid Sequence*

MVRKKNPPLRNVASEGEGQILEPIGTESKVSGKNKEFSADQMSENTDQSDAAELNHKEEHSLHVQDPSSS
SKKDLKSAVLSEKAGFNYESPSKGGNFPSFPHDEVTDRNMLAFSFPAAGGVCEPLKSPQRAEADDPQDMA
CTPSGDSLETKEDQKMSPKATEETGQAQSGQANCQGLSPVSVASKNPQVPSDGGVRLNKSKTDLLVNDNP
DPAPLSPELQDFKCNICGYGYYGNDPTDLIKHFRKYHLGLHNRTRQDAELDSKILALHNMVQFSHSKDFQ
KVNRSVFSGVLQDINSSRPVLLNGTYDVQVTSGGTFIGIGRKTPDCQGNTKYFRCKFCNFTYMGNSSTEL
EQHFLQTHPNKIKASLPSSEVAKPSEKNSNKSIPALQSSDSGDLGKWQDKITVKAGDDTPVGYSVPIKPL
DSSRQNGTEATSYYWCKFCSFSCESSSSLKLLEHYGKQHGAVQSGGLNPELNDKLSRGSVINQNDLAKSS
EGETMTKTDKSSSGAKKKDFSSKGAEDNMVTSYNCQFCDFRYSKSHGPDVIVVGPLLRHYQQLHNIHKCT
IKHCPFCPRGLCSPEKHLGEITYPFACRKSNCSHCALLLLHLSPGAAGSSRVKHQCHQCSFTTPDVDVLL
PHYESVHESQASDVKQEANHLQGSDGQQSVKESKEHSCTKCDFITQVEEEISRHYRRAHSCYKCRQCSFT
AADTQSLLEHFNTVHCQEQDITTANGEEDGHAISTIKEEPKIDFRVYNLLTPDSKMGEPVSESVVKREKL
EEKDGLKEKVWTESSSDDLRNVTWRGADILRGSPSYTQASLGLLTPVSGTQEQTKTLRDSPNVEAAHLAR
PIYGLAVETKGFLQGAPAGGEKSGALPQQYPASGENKSKDESQSLLRRRGSGVFCANCLTTKTSLWRKN
ANGGYVCNACGLYQKLHSTPRPLNIIKQNNGEQIIRRRTKRLNPEALQAEQLNKQQRGSNEEQVNGSPL
ERRSEDHLTESHQREIPLPSLSKYEAQGSLTKSHSAQQPVLVSQTLDIHKRMQPLHIQIKSPQESTGDPG
NSSSVSEGKGSSERGSPIEKYMRPAKHPNYSPPGSPIEKYQYPLFGLPFVHNDFQSEADWLRFWSKYKLS
VPGNPHYLSHVPGLPNPCQNYVPYPTFNLPPHFSAVGSDNDIPLDLAIKHSRPGPTANGASKEKTKAPPN
VKNEGPLNVVKTEKVDRSTQDELSTKCVHCGIVFLDEVMYALHMSCHGDSGPFQCSICQHLCTDKYDFTT
HIQRGLHRNNAQVEKNGKPKE

FIGURE 3

A. BCY1 cDNA Sequence

```
TGCAAGATTAAGGCCTTGAGGGCCAAGACCAACACCTACATCAAGACACCGGTGAGGGGCGAGGAACCAGTGTTCATG
GTGACAGGGCGACGGGAGGACGTGGCCACAGCCCGGCGGGAAATCATCTCAGCAGCGGAGCACTTCTCCATGATCCGT
GCCTCCCGCAACAAGTCAGGCGCCGCCTTTGGTGTGGCTCCTGCTCTGCCCGGCCAGGTGACCATCCGTGTGCGGGTG
CCCTACCGCGTGGTGGGGCTGGTGGTGGGCCCCAAAGGGGCAACCATCAAGCGCATCCAGCAGCAAACCAACACATAC
ATTATCACACCAAGCCGTGACCGCGACCCCGTGTTCGAGATCACGGGTGCCCCAGGCAACGTGGAGCGTGCGCGCGAG
GAGATCGAGACGCACATCGCGGTGCGCACTGGCAAGATCCTCGAGTACAACAATGAAAACGACTTCCTGGCGGGGAGC
CCCGACGCAGCAATCGATAGCCGCTACTCCGACGCCTGGCGGGTGCACCAGCCCGGCTGCAAGCCCCTCTCCACCTTC
CGGCAGAACAGCCTGGGCTGCATCGGCGAGTGCGGAGTGGACTCTGGCTTTGAGGCCCCACGCCTGGGTGAGCAGGGC
GGGGACTTTGGCTACGGCGGGTACCTCTTTCCGGGCTATGGCGTGGGCAAGCAGGATGTGTACTACGGCGTGGCCGAG
ACTAGCCCCCGCTGTGGGCGGGCAGGAGAACGCCACGCCCACCTCCGTGCTCTTCTCCTCYKCCTCCTCCTCCTCC
TCCTCTTCCGCCAAGGCCCGCGCTGGGCCCCGGGCGCACACCGCTCCCTGCCACTTCCGCGGGACCCGAGCTGGCC
GGACTCCCGAGGCGCCCCCGGGAGAGCCGCTCCRGGGCTTCTCTAAACTTGGTGGGGGCGGCCTGCGGAGCCCCGCA
GCCGGCGGGCGGGATTGCATGGTCTGCTTTGAGAGCGAAGTGACTGCCGCCCTTGTGCCCTGCGGACACAACCTGTTC
TGCATGGAGTGTGCAGTACGCATCTGCGAGAGGACGGACCCAGAGTGTCCCGTCTGCCACATCACAGCCACGCAAGCC
ATCCGAATATTCTCCTAAGCCCCGTGCCCCATGCCTCCGGGGCCCACTCCACTGGGCCCACCCTGGACCTGTTTTCCA
CTAAAGCCTTTTGGAAAGCGGTGATTTGAGGGGCAAGGTGCTTAGAGATACTCGCTCGCTGGGGAAGGGGGGAGGGAG
GCAGTGGTGGCTGGAGGGTGCGCCACTTTCAGAGCCTCTGGTCACCCTGTCCTGGAAAGATTGGGAGGGGGCCAGACT
GAAAATTTTACTAGAGTTACAACTCTGATACCTCAACACACCCTTAAATCTGGAAGCAGCTAAGAGAAACTTTTGTTT
TGCCAGAGGTGGCCACTAAGGCATTCTGACGCCCTCTGCCCACCTCCCCGCTGTGTGTCACTCCACCCCTTCTTCCG
AGGAGGGGGTGGGTAAAAGGGAGAGGGAGAATTACCACCTGTATCTAGAGGTGCTCTTTGCAATCCCTAAGCCCTCTG
GTCCTGACCTCCGACCTCCCAGCTCTGTCTTGTTCCTTGTCTTTGTCTTTCTTCCCTTCCCCCTGCCCCTGCCCCTAC
CAGCCCAGCTTTGGGGACACCATCCTTCTGGGGAGAAGTAGGGGGAGGAATATTTGGATGGTCCCTCCATTCCTCTTC
AGGCATCTGGAGGCCCTCTCCCCCACTCCTCCAAAGAAACATCTCAAATTATTGATGGAATGTATCCCCATTCTCAGT
GAAAATGTGAGGAGGGGACTAATACTGGGGTAAAGGGTCAAACCCCCACCTTCATCACTATGGGCATTATATTTAGGG
AGTAGTTCTTGGGCTGGATTTTCTGGTTGTGGAAGTGGGGCGCCAGAGTAGTGTGTCTGCTATTTAAAGGAGCAGGA
AAGGGCGTGAGGCAGGAGGAGAGACTGGTGGAGGGAAGAGCTGCTCCTCCCATGCAGTGCCCGACTCCCTGCACCCCT
CTCAACCTGACCTGAACCTTTATTGAATCCTTATTAGCTTGAATCCTTATTAGCTTGAATCCTCCATGCAAATCATGG
AGTCTGTGTCCCACCTGATGTGGTTGAGGAGAAGCCAGGTCTTCAAAGAGGGGTCAGCCTGGGCAAAGCAGGACTGG
GGGGAGGTGGGCAGCAGGGCCTATTCTGAGAATCACATATTGTTACAGGCCTTGCACCCCCTTTGCTGCTTCCCTCCT
GCTCATTTGGGGCTGCCACCAGCTCTCCACCCTCCTGGTTCCGCTGGCCGGGCCAAGAGAGGATGGAGGGATGGGAGT
CCCAGGAGATCCTTGTAAATAGTGGGGTGGGACTGTTCTGAGTGATCACCCCGAGCACTTAAAGCTCCAGAGTCCCATT
CTTCCTGGATGGAGCAGGTGGAGGTGCAGAGGGGATTTCCTCCTCTCCTTCCTCCTGTCGAGAATTAACACCTCTCCA
CAGCCTTCCCCTCCAGAACACCAGCCAGGGAGGGGTGGGGAAGGAGGTCACAGCCAAGAAAACTGCCCTGTGACGACT
TCCCTCCTTCCCGCCTATGTGAGCCATCCTGAGATGTCTGTACAATAGAAACCAAACCAAATGGGCACCCTCGGTTGC
CGGGGGGCAGGTGGGGAGGGGGGTGGGAAGAAGGGATGTCTGTCTGTCGTCCCCCTCCCCCTCTCCACTCTTTACCCA
CAAAGGCAGAAGACTGTTACACTAGGGGCTCAGCAAATTCAATCCCACCCTTACCAATTGAGCCAAACCTAGAAACA
AACACAAAACACGAATAGTGAGAGACAAAATAGAGGAGAGAAAGAGAGCATGAGAGGGAGCGAGACAGGCGACCAACA
CAGAGGAGAGAAAACAAAAATAGCAAAAAAAAAAAAAAAAA
```

B. BCY1 Amino Acid Sequence

```
MAELRLKGSS  NTTECVPVPT  SEHVAEIVGR  QGCKIKALRA  KTNTYIKTPV  RGEEPVFMVT
GRREDVATAR  REIISAAEHF  SMIRASRNKS  GAAFGVAPAL  PGQVTIRVRV  PYRVVGLVVG
PKGATIKRIQ  QQTNTYIITP  SRDRDPVFEI  TGAPGNVERA  REEIETHIAV  RTGKILEYNN
ENDFLAGSPD  AAIDSRYSDA  WRVHQPGCKP  LSTFRQNSLG  CIGECGVDSG  FEAPRLGEQG
GDFGYGGYLF  PGYGVGKQDV  YYGVAETSPP  LWAGQENATP  TSVLFSSASS  SSSSSAKARA
GPPGAHRSPA  TSAGPELAGL  PRRPPGEPLQ  GFSKLGGGGL  RSPGGGRDCM
VCFESEVTAA  LVPCGHNLFC  MECAVRICER  TDPECPVCHI  TAAQAIRIFS
```

FIGURE 4

```
ATGACAAAGAGGAAGAAGACCATCAACCTTAATATACAAGACGCCCAGAAGAGGACTGCTCTACACTGGGCCTGTGTC
AATGGCCATGAGGAAGTAGTAACATTTCTGGTAGACAGAAAGTGCCAGCTTGACGTCCTTGATGGCGAACACAGGACA
CCTCTGATGAAGGCTCTACAATGCCATCAGGAGGCTTGTGCAAATATTCTGATAGATTCTGGTGCCGATATAAATCTC
GTAGATGTGTATGGCAACATGGCTCTCCATTATGCTGTTTATAGTGAGATTTTGTCAGTGGTGGCAAAACTGCTGTCC
CATGGTGCAGTCATCGAAGTGCACAACAAGGCTAGCCTCACACCACTTTTACTATCCATAACGAAAAGAAGTGAGCAA
ATTGTGGAATTTTTGCTGATAAAAAATGCAAATGCGAATGCAGTTAATAAGTATAAATGCACAGCCCTCATGCTTGCT
GTATGTCATGGATCATCAGAGATAGTTGGCATGCTTCTTCAGCAAAATGTTGACGTCTTTGCTGCAGATATATGTGGA
GTAACTGCAGAACATTATGCTGTTACTTGTGGATTTCATCACATTCATGAACAAATTATGGAATATATACGAAAATTA
TCTAAAAATCATCAAAATACCAATCCAGAAGGAACATCTGCAGGAACACCTGATGAGGCTGCACCCTTGGCGGAAAGA
ACACCTGACACAGCTGAAAGCTTGGTGGAAAAAACACCTGATGAGGCTGCACCCTTGGTGGAAAGAACACCTGACACG
GCTGAAAGCTTGGTGGAAAAAACACCTGATGAGGCTGCATCCTTGGTGGAGGGAACATCTGACAAAATTCAATGTTTG
GAGAAAGCGACATCTGGAAAGTTCGAACAGTCAGCAGAAGAAACACCTAGGGAAATTACGAGTCCTGCAAAAGAAACA
TCTGAGAAATTTACGTGGCCAGCAAAAGGAAGACCTAGGAAGATCGCATGGGAGAAAAAAGAAGACACACCTAGGGAA
ATTATGAGTCCCGCAAAAGAAACATCTGAGAAATTTACGTGGGCAGCAAAAGGAAGACCTAGGAAGATCGCATGGGAG
AAAAAAGAAACACCTGTAAAGACTGGATGCGTGGCAAGAGTAACATCTAATAAAACTAAAGTTTTGGAAAAAGGAAGA
TCTAAGATGATTGCATGTCCTACAAAAGAATCATCTACAAAAGCAAGTGCCAATGATCAGAGGTTCCCATCAGAATCC
AAACAAGAGGAAGATGAAGAATATTCTTGTGATTCTCGGAGTCTCTTTGAGAGTTCTGCAAAGATTCAAGTGTGTATA
CCTGAGTCTATATATCAAAAAGTAATGGAGATAAATAGAGAAGTAGAAGAGCCTCCTAAGAAGCCATCTGCCTTCAAG
CCTGCCATTGAAATGCAAAACTCTGTTCCAAATAAAGCCTTTGAATTGAAGAATGAACAAACATTGAGAGCAGATCCG
ATGTTCCCACCAGAATCCAAACAAAAGGACTATGAAGAAAATTCTTGGGATTCTGAGAGTCTCTGTGAGACTGTTTCA
CAGAAGGATGTGTGTTTACCCAAGGCTACACATCAAAAAGAAATAGATAAAATAAATGGAAAATTAGAAGAGTCTCCT
AATAAAGATGGTCTTCTGAAGGCTACCTGCCGGAATGAAAGTTTCTATTCCAACTAAAGCCTTAGAATTGAAGGACATG
CAAACTTTCAAAGCGGAGCCTCCGGGGAAGCCATCTGCCTTCGAGCCTGCCACTGAAATGCAAAAGTCTGTCCCAAAT
AAAGCCTTGGAATTGAAAAATGAACAAACATGGAGAGCAGATGAGATACTCCCATCAGAATCCAAACAAAAGGACTAT
GAAGAAATTCTTGGGATACTGAGAGTCTCTGTGAGACTGTTTCACAGAAGGATGTGTGTTTACCCAAGGCTGCGCAT
CAAAAAGAAATAGATAAAATAAATGGAAAATTAGAAGGGTCTCCTGTTAAAGATGGTCTTCTGAAGGCTAACTGCGGA
ATGAAAGTTTCTATTCCAACTAAAGCCTTAGAATTGATGGACATGCAAACTTTCAAAGCAGAGCCTCCCGAGAAGCCA
TCTGCCTTCGAGCCTGCCATTGAAATGCAAAAGTCTGTTCCAAATAAAGCCTTGGAATTGAAGAATGAACAAACATTG
AGAGCAGATGAGATACTCCCATCAGAATCCAAACAAAAGGACTATGAAGAAAGTTCTTGGGATTCTGAGAGTCTCTGT
GAGACTGTTTCACAGAAGGATGTGTGTTTACCCAAGGCTACACATCAAAAAGAAATAGATAAAATAAATGGAAAATTA
GAAGAGTCTCCTGATAATGATGGTTTTCTGAAGGCTCCCTGCAGAATGAAAGTTTCTATTCCAACTAAAGCCTTAGAA
TTGATGGACATGCAAACTTTCAAAGCAGAGCCTCCCGAGAAGCCATCTGCCTTCGAGCCTGCCATTGAAATGCAAAAG
TCTGTTCCAAATAAAGCCTTGGAATTGAAGAATGAACAAACATTGAGAGCAGATCAGATGTTCCCTTCAGAATCAAAA
CAAAAGAAGGTTGAAGAAATTCTTGGGATTCTGAGAGTCTCCGTGAGACTGTTTCACAGAAGGATGTGTGTGTACCC
AAGGCTACACATCAAAAGAAATGGATAAAATAAGTGGAAATTAGAAGATTCAACTAGCCTATCAAAAATCTTGGAT
ACAGTTCATTCTTGTGAAAGAGCAAGGGAACTTCAAAAAGATCACTGTGAACAACGTACAGGAAAATGGAACAAATG
AAAAAGAAGTTTTGTGTACTGAAAAGAAACTGTCAGAAGCAAAAGAAATAAAATCACAGTTAGAGAACCAAAAAGTT
AAATGGGAACAAGAGCTCTGCAGTGTGAGATTGACTTTAAACCAAGAAGAAGAGAAGAGAAGAAATGCCGATATATTA
AATGAAAAAATTAGGGAAGAATTAGGAAGAATCGAAGAGCAGCATAGGAAAGAGTTAGAAGTGAAACAACAACTTGAA
CAGGCTCTCAGAATACAAGATATAGAATTGAAGAGTGTAGAAAGTAATTTGAATCAGGTTTCTCACACTCATGAAAAT
GAAAATTATCTCTTACATGAAATTGCATGTTGAAAAAGGAAATTGCCATGCTAAAACTGGAAATAGCCACACTGAAA
CACCAATACCAGGAAAAGGAAAATAAATACTTTGAGGACATTAAGATTTTAAAAGAAAAGAATGCTGAACTTCAGATG
ACCCTAAAACTGAAAGAGGAATCATTAACTAAAAGGGCATCTCAATATAGTGGGCAGCTTAAAGTTCTGATAGCTGAG
AACACAATGCTCACTTCTAAATTGAAGGAAAAACAAGACAAAGAAATACTAGAGGCAGAAATTGAATCACACCATCCT
AGACTGGCTTCTGCTGTACAAGACCATGATCAAATTGTGACATCAAGAAAAAGTCAAGAACCTGCTTTCCACATTGCA
GGAGATGCTTGTTTGCAAAGAAAATGAATGTTGATGTGAGTAGTACGATATATAACAATGAGGTGCTCCATCAACCA
CTTTCTGAAGCTCAAAGGAAATCCAAAAGCCTAAAAATTAATCTCAATTATGCAGGAGATGCTCTAAGAGAAAATACA
TTGGTTTCAGAACATGCACAAAGAGACCAACGTGAAACACAGTGTCAAATGAAGGAAGCTGAACACATGTATCAAAAC
GAACAAGATAATGTGAACAAACACACTGAACAGCAGGAGTCTCTAGATCAGAAATTATTTCAACTACAAAGCAAAAAT
ATGTGGCTTCAACAGCAATTAGTTCATGCACATAAGAAAGCTGACAACAAAAGCAAGATAACAATTGATATTCATTTT
CTTGAGAGGAAAATGCAACATCATCTCCTAAAAGAGAAAAATGAGGAGATATTTAATTACAATAACCATTTAAAAAAC
CGTATATATCAATATGAAAAGAGAAAGCAGAAACAGAAAACTCATGA
```

FIGURE 5

MTKRKKTINLNIQDAQKRTALHWACVNGHEEVVTFLVDRKCQLDVLDGEHRTPLMKALQCHQEACANILIDSGADINL
VDVYGNMALHYAVYSEILSVVAKLLSHGAVIEVHNKASLTPLLLSITKRSEQIVEFLLIKNANANAVNKYKCTALMLA
VCHGSSEIVGMLLQQNVDVFAADICGVTAEHYAVTCGFHHIHEQIMEYIRKLSKNHQNTNPEGTSAGTPDEAAPLAER
TPDTAESLVEKTPDEAAPLVERTPDTAESLVEKTPDEAASLVEGTSDKIQCLEKATSGKFEQSAEETPREITSPAKET
SEKFTWPAKGRPRKIAWEKKEDTPREIMSPAKETSEKFTWAAKGRPRKIAWEKKETPVKTGCVARVTSNKTKVLEKGR
SKMIACPTKESSTKASANDQRFPSESKQEEDEEYSCDSRSLFESSAKIQVCIPESIYQKVMEINREVEEPPKKPSAFK
PAIEMQNSVPNKAFELKNEQTLRADPMFPPESKQKDYEENSWDSESLCETVSQKDVCLPKATHQKEIDKINGKLEESP
NKDGLLKATCGMKVSIPTKALELKDMQTFKAEPPGKPSAFEPATEMQKSVPNKALELKNEQTWRADEILPSESKQKDY
EENSWDTESLCETVSQKDVCLPKAAHQKEIDKINGKLEGSPVKDGLLKANCGMKVSIPTKALELMDMQTFKAEPPEKP
SAFEPAIEMQKSVPNKALELKNEQTLRADEILPSESKQKDYEESSWDSESLCETVSQKDVCLPKATHQKEIDKINGKL
EESPDNDGFLKAPCRMKVSIPTKALELMDMQTFKAEPPEKPSAFEPAIEMQKSVPNKALELKNEQTLRADQMFPSESK
QKKVEENSWDSESLRETVSQKDVCVPKATHQKEMDKISGKLEDSTSLSKILDTVHSCERARELQKDHCEQRTGKMEQM
KKKFCVLKKKLSEAKEIKSQLENQKVKWEQELCSVRLTLNQEEEKRRNADILNEKIREELGRIEEQHRKELEVKQQLE
QALRIQDIELKSVESNLNQVSHTHENENYLLHENCMLKKEIAMLKLEIATLKHQYQEKENKYFEDIKILKEKNAELQM
TLKLKEESLTKRASQYSGQLKVLIAENTMLTSKLKEKQDKEILEAEIESHHPRLASAVQDHDQIVTSRKSQEPAFHIA
GDACLQRKMNVDVSSTIYNNEVLHQPLSEAQRKSKSLKINLNYAGDALRENTLVSEHAQRDQRETQCQMKEAEHMYQN
EQDNVNKHTEQQESLDQKLFQLQSKNMWLQQQLVHAHKKADNKSKITIDIHFLERKMQHHLLKEKNEEIFNYNNHLKN
RIYQYEKEKAETENS

US 8,021,664 B2

TUMOR ANTIGENS BFA5 FOR PREVENTION AND/OR TREATMENT OF CANCER

RELATED APPLICATIONS

This application claims priority to U.S. Provisional Application No. 60/462,945 filed Apr. 15, 2003.

FIELD OF THE INVENTION

The present invention relates to a nucleic acid encoding a polypeptide and the use of the nucleic acid or polypeptide in preventing and/or treating cancer. In particular, the invention relates to improved vectors for the insertion and expression of foreign genes encoding tumor antigens for use in immunotherapeutic treatment of cancer.

BACKGROUND OF THE INVENTION

There has been tremendous increase in last few years in the development of cancer vaccines with Tumour-associated antigens (TAAs) due to the great advances in identification of molecules based on the expression profiling on primary tumours and normal cells with the help of several techniques such as high density microarray, SEREX, immunohistochemistry (IHC), RT-PCR, in-situ hybridization (ISH) and laser capture microscopy (Rosenberg, Immunity, 1999; Sgroi et al, 1999, Schena et al, 1995, Offringa et al, 2000). The TAAs are antigens expressed or over-expressed by tumour cells and could be specific to one or several tumours for example CEA antigen is expressed in colorectal, breast and lung cancers. Sgroi et al. (1999) identified several genes differentially expressed in invasive and metastatic carcinoma cells with combined use of laser capture microdissection and cDNA microarrays. Several delivery systems like DNA or viruses could be used for therapeutic vaccination against human cancers (Bonnet et al, 2000) and can elicit immune responses and also break immune tolerance against TAAs. Tumour cells can be rendered more immunogenic by inserting transgenes encoding T cell co-stimulatory molecules such as B7.1 or cytokines such as IFN-γ, IL2, or GM-CSF, among others. Co-expression of a TAA and a cytokine or a co-stimulatory molecule has also been shown to be useful in developing effective therapeutic vaccines (Hodge et al, 95, Bronte et al, 1995, Chamberlain et al, 1996).

There is a need in the art for reagents and methodologies useful in stimulating an immune response to prevent or treat cancers. The present invention provides such reagents and methodologies which overcome many of the difficulties encountered by others in attempting to treat cancer.

SUMMARY OF THE INVENTION

The present invention provides an immunogenic target for administration to a patient to prevent and/or treat cancer. In particular, the immunogenic target is a tumor antigen ("TA") and/or an angiogenesis-associated antigen ("AA"). In one embodiment, the immunogenic target is encoded by SEQ ID NO.: 5 or has the amino acid sequence of SEQ ID NO.: 6. In certain embodiments, the TA and/or AA are administered to a patient as a nucleic acid contained within a plasmid or other delivery vector, such as a recombinant virus. The TA and/or AA may also be administered in combination with additional tumor antigens (i.e., SEQ ID NOS.: 1-4) and/or an immune stimulator, such as a co-stimulatory molecule or adjuvant.

BRIEF DESCRIPTION OF THE DRAWINGS

FIG. 1. BFA4 cDNA sequence (SEQ ID NO.:1).
FIG. 2. BFA4 amino acid sequence (SEQ ID NO.:2).
FIG. 3. BCY1 nucleotide (A; SEQ ID NO.:3) and amino acid (B; SEQ ID NO.:4) sequences.
FIG. 4. BFA5 cDNA sequence (SEQ ID NO.:5).
FIG. 5. BFA5 amino acid sequence (SEQ ID NO.:6).

DETAILED DESCRIPTION

The present invention provides reagents and methodologies useful for treating and/or preventing cancer. All references cited within this application are incorporated by reference.

In one embodiment, the present invention relates to the induction or enhancement of an immune response against one or more tumor antigens ("TA") to prevent and/or treat cancer. In certain embodiments, one or more TAs may be combined. In preferred embodiments, the immune response results from expression of a TA in a host cell following administration of a nucleic acid vector encoding the tumor antigen or the tumor antigen itself in the form of a peptide or polypeptide, for example.

As used herein, an "antigen" is a molecule such as a polypeptide or a portion thereof that produces an immune response in a host to whom the antigen has been administered. The immune response may include the production of antibodies that bind to at least one epitope of the antigen and/or the generation of a cellular immune response against cells expressing an epitope of the antigen. The response may be an enhancement of a current immune response by, for example, causing increased antibody production, production of antibodies with increased affinity for the antigen, or an increased or more effective cellular response (i.e., increased T cells or T cells with higher anti-tumor activity). An antigen that produces an immune response may alternatively be referred to as being immunogenic or as an, immunogen. In describing the present invention, a TA may be referred to as an "immunogenic target".

TA includes both tumor-associated antigens (TAAs) and tumor-specific antigens (TSAs), where a cancerous cell is the source of the antigen. A TAA is an antigen that is expressed on the surface of a tumor cell in higher amounts than is observed on normal cells or an antigen that is expressed on normal cells during fetal development. A TSA is an antigen that is unique to tumor cells and is not expressed on normal cells. TA further includes TAAs or TSAs, antigenic fragments thereof, and modified versions that retain their antigenicity.

TAs are typically classified into five categories according to their expression pattern, function, or genetic origin: cancertestis (CT) antigens (i.e., MAGE, NY-ESO-1); melanocyte differentiation antigens (i.e., Melan A/MART-1, tyrosinase, gp100); mutational antigens (i.e., MUM-1, p53, CDK-4); overexpressed 'self' antigens (i.e., HER-2/neu, p53); and, viral antigens (i.e., HPV, EBV). For the purposes of practicing the present invention, a suitable TA is any TA that induces or enhances an anti-tumor immune response in a host in whom the TA is expressed. Suitable TAs include, for example, gp100 (Cox et al., Science, 264:716-719 (1994)), MART-1/Melan A (Kawakami et al., J. Exp. Med., 180:347-352 (1994)), gp75 (TRP-1) (Wang et al., J. Exp. Med., 186: 1131-1140 (1996)), tyrosinase (Wolfel et al., Eur. J. Immunol., 24:759-764 (1994); WO 200175117; WO 200175016; WO 200175007), NY-ESO-1 (WO 98/14464; WO 99/18206), melanoma proteoglycan (Hellstrom et al., J. Immunol., 130:1467-1472 (1983)), MAGE family antigens (i.e., MAGE-1, 2, 3, 4, 6, 12, 51; Van der Bruggen et al., Science, 254:1643-1647 (1991); U.S. Pat. No. 6,235,525; CN 1319611), BAGE family antigens (Boel et al., Immunity, 2:167-175 (1995)), GAGE family antigens (i.e., GAGE-1,2;

Van den Eynde et al., *J. Exp. Med.*, 182:689-698 (1995); U.S. Pat. No. 6,013,765), RAGE family antigens (i.e., RAGE-1; Gaugler et al., *Immunogenetics*, 44:323-330 (1996); U.S. Pat. No. 5,939,526), N-acetylglucosaminyltransferase-V (Guilloux et al., *J. Exp. Med.*, 183:1173-1183 (1996)), p15 (Robbins et al., *J. Immunol.* 154:5944-5950 (1995)), β-catenin (Robbins et al., *J. Exp. Med.*, 183:1185-1192 (1996)), MUM-1 (Coulie et al., *Proc. Natl. Acad. Sci.* USA, 92:7976-7980 (1995)), cyclin dependent kinase-4 (CDK4) (Wolfel et al., *Science*, 269:1281-1284 (1995)), p21-ras (Fossum et al., *Int. J. Cancer*, 56:40-45 (1994)), BCR-abl (Bocchia et al., *Blood*, 85:2680-2684 (1995)), p53 (Theobald et al., *Proc. Natl. Acad. Sci.* USA, 92:11993-11997 (1995)), p185 HER2/neu (erb-B1; Fisk et al., *J. Exp. Med.*, 181:2109-2117 (1995)), epidermal growth factor receptor (EGFR) (Harris et al., *Breast Cancer Res. Treat*, 29:1-2 (1994)), carcinoembryonic antigens (CEA) (Kwong et al., *J. Natl. Cancer Inst.*, 85:982-990 (1995) U.S. Pat. Nos. 5,756,103; 5,274,087; 5,571,710; 6,071,716; 5,698,530; 6,045,802; EP 263933; EP 346710; and, EP 784483); carcinoma-associated mutated mucins (i.e., MUC-1 gene products; Jerome et al., *J. Immunol.*, 151:1654-1662 (1993)); EBNA gene products of EBV (i.e., EBNA-1; Rickinson et al., *Cancer Surveys*, 13:53-80 (1992)); E7, E6 proteins of human papillomavirus (Ressing et al., *J. Immunol.* 154:5934-5943 (1995)); prostate specific antigen (PSA; Xue et al., *The Prostate*, 30:73-78 (1997)); prostate specific membrane antigen (PSMA; Israeli, et al., *Cancer Res.*, 54:1807-1811 (1994)); idiotypic epitopes or antigens, for example, immunoglobulin idiotypes or T cell receptor idiotypes (Chen et al., *J. Immunol.*, 153:4775-4787 (1994)); KSA (U.S. Pat. No. 5,348,887), kinesin 2 (Dietz, et al. Biochem Biophys Res Commun 2000 Sep. 7; 275(3):731-8), HIP-55, TGFβ-1 antiapoptotic factor (Toomey, et al. Br J Biomed Sci 2001; 58(3): 177-83), tumor protein D52 (Bryne J. A., et al., Genomics, 35:523-532 (1996)), H1FT, NY-BR-1 (WO 01/47959), NY-BR-62, NY-BR-75, NY-BR-85, NY-BR-87, NY-BR-96 (Scanlan, M. Serologic and Bioinformatic Approaches to the Identification of Human Tumor Antigens, in *Cancer Vaccines 2000*, Cancer Research Institute, New York, N.Y.), BFA4 (SEQ ID NOS.: 1 and 2), BCY1 (SEQ ID NOS.: 3 and 4), and BFA5 (SEQ ID NOS.: 5 and 6) including "wild-type" (i.e., normally encoded by the genome, naturally-occurring), modified, and mutated versions as well as other fragments and derivatives thereof. Any of these TAs may be utilized alone or in combination with one another in a co-immunization protocol.

In certain cases, it may be beneficial to co-immunize patients with both TA and other antigens, such as angiogenesis-associated antigens ("AA"). An AA is an immunogenic molecule (i.e., peptide, polypeptide) associated with cells involved in the induction and/or continued development of blood vessels. For example, an AA may be expressed on an endothelial cell ("EC"), which is a primary structural component of blood vessels. For treatment of cancer, it is preferred that that the AA be found within or near blood vessels that supply a tumor. Immunization of a patient against an AA preferably results in an anti-AA immune response whereby angiogenic processes that occur near or within tumors are prevented and/or inhibited.

Exemplary AAs include, for example, vascular endothelial growth factor (i.e., VEGF; Bernardini, et al. *J. Urol.*, 2001, 166(4): 1275-9; Starnes, et al. *J. Thorac. Cardiovasc. Surg.*, 2001, 122(3): 518-23; Dias, et al. *Blood*, 2002, 99: 2179-2184), the VEGF receptor (i.e., VEGF-R, flk-1/KDR; Starnes, et al. *J. Thorac. Cardiovasc. Surg.*, 2001, 122(3): 518-23), EPH receptors (i.e., EPHA2; Gerety et al. 1999, *Cell*, 4: 403-414), epidermal growth factor receptor (i.e., EGFR; Ciardeillo, et al. *Clin. Cancer Res.*, 2001, 7(10): 2958-70), basic fibroblast growth factor (i.e., bFGF; Davidson, et al. *Clin. Exp. Metastasis* 2000, 18(6): 501-7; Poon, et al. Am J. Surg., 2001, 182(3):298-304), platelet-derived cell growth factor (i.e., PDGF-B), platelet-derived endothelial cell growth factor (PD-ECGF; Hong, et al. *J. Mol. Med.*, 2001, 8(2):141-8), transforming growth factors (i.e., TGF-α; Hong, et al. *J. Mol. Med.*, 2001, 8(2):141-8), endoglin (Balza, et al. *Int. J. Cancer*, 2001, 94: 579-585), Id proteins (Benezra, R. Trends Cardiovasc. Med., 2001, 11(6):237-41), proteases such as uPA, uPAR, and matrix metalloproteinases (MMP-2, MMP-9; Djonov, et al. J. Pathol., 2001, 195(2):147-55), nitric oxide synthase (Am. J. Opthalmol., 2001, 132(4):551-6), aminopeptidase (Rouslhati, E. Nature Cancer, 2: 84-90, 2002), thrombospondins (i.e., TSP-1, TSP-2; Alvarez, et al. Gynecol. Oncol., 2001, 82(2):273-8; Seki, et al. Int. J. Oncol., 2001, 19(2):305-10), k-ras (Zhang, et al. Cancer Res., 2001, 61(16):6050-4), Wnt (Zhang, et al. Cancer Res., 2001, 61(16):6050-4), cyclin-dependent kinases (CDKs; Drug Resist. Updat. 2000, 3(2):83-88), microtubules (Timar, et al. 2001. *Path. Oncol. Res.*, 7(2): 85-94), heat shock proteins (i.e., HSP90 (Timar, supra)), heparin-binding factors (i.e., heparinase; Gohji, et al. Int. J. Cancer, 2001, 95(5):295-301), synthases (i.e., ATP synthase, thymidilate synthase), collagen receptors, integrins (i.e., αvβ3, αvβ5, α1β1, α2β1, α5β1), the surface proteolglycan NG2, AAC2-1 (SEQ ID NO.:1), or AAC2-2 (SEQ ID NO.:2), among others, including "wild-type" (i.e., normally encoded by the genome, naturally-occurring), modified, mutated versions as well as other fragments and derivatives thereof. Any of these targets may be suitable in practicing the present invention, either alone or in combination with one another or with other agents.

In certain embodiments, a nucleic acid molecule encoding an immunogenic target is utilized. The nucleic acid molecule may comprise or consist of a nucleotide sequence encoding one or more immunogenic targets, or fragments or derivatives thereof, such as that contained in a DNA insert in an ATCC Deposit. The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, among others.

An isolated nucleic acid molecule is one that: (1) is separated from at least about 50 percent of proteins, lipids, carbohydrates, or other materials with which it is naturally found when total nucleic acid is isolated from the source cells; (2) is not linked to all or a portion of a polynucleotide to which the nucleic acid molecule is linked in nature; (3) is operably linked to a polynucleotide which it is not linked to in nature; and/or, (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use. As used herein, the term "naturally occurring" or "native" or "naturally found" when used in connection with biological materials such as nucleic acid molecules, polypeptides, host cells, and the like, refers to materials which are found in nature without manipulation by man. Similarly, "non-naturally occurring" or "non-native" as used herein refers to a material that is not found in nature or that has been structurally modified or synthesized by man.

The identity of two or more nucleic acid or polypeptide molecules is determined by comparing the sequences. As known in the art, "identity" means the degree of sequence relatedness between nucleic acid molecules or polypeptides as determined by the match between the units making up the molecules (i.e., nucleotides or amino acid residues). Identity measures the percent of identical matches between the smaller of two or more sequences with gap alignments (if any) addressed by a particular mathematical model or computer program (i.e., an algorithm). Identity between nucleic acid sequences may also be determined by the ability of the related sequence to hybridize to the nucleic acid sequence or isolated nucleic acid molecule. In defining such sequences, the term "highly stringent conditions" and "moderately stringent conditions" refer to procedures that permit hybridization of nucleic acid strands whose sequences are complementary, and to exclude hybridization of significantly mismatched nucleic acids. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. (see, for example, Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited)). The term "moderately stringent conditions" refers to conditions under which a DNA duplex with a greater degree of base pair mismatching than could occur under "highly stringent conditions" is able to form. Exemplary moderately stringent conditions are 0.015 M sodium chloride, 0.0015 M sodium citrate at 50-65° C. or 0.015 M sodium chloride, 0.0015 M sodium citrate, and 20% formamide at 37-50° C. By way of example, moderately stringent conditions of 50° C. in 0.015 M sodium ion will allow about a 21% mismatch. During hybridization, other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH.

In certain embodiments of the present invention, vectors are used to transfer a nucleic acid sequence encoding a polypeptide to a cell. A vector is any molecule used to transfer a nucleic acid sequence to a host cell. In certain cases, an expression vector is utilized. An expression vector is a nucleic acid molecule that is suitable for transformation of a host cell and contains nucleic acid sequences that direct and/or control the expression of the transferred nucleic acid sequences. Expression includes, but is not limited to, processes such as transcription, translation, and splicing, if introns are present. Expression vectors typically comprise one or more flanking sequences operably linked to a heterologous nucleic acid sequence encoding a polypeptide. Flanking sequences may be homologous (i.e., from the same species and/or strain as the host cell), heterologous (i.e., from a species other than the host cell species or strain), hybrid (i.e., a combination of flanking sequences from more than one source), or synthetic, for example.

A flanking sequence is preferably capable of effecting the replication, transcription and/or translation of the coding sequence and is operably linked to a coding sequence. As used herein, the term operably linked refers to a linkage of polynucleotide elements in a functional relationship. For instance, a promoter or enhancer is operably linked to a coding sequence if it affects the transcription of the coding sequence. However, a flanking sequence need not necessarily be contiguous with the coding sequence, so long as it functions correctly. Thus, for example, intervening untranslated yet transcribed sequences can be present between a promoter sequence and the coding sequence and the promoter sequence may still be considered operably linked to the coding sequence. Similarly, an enhancer sequence may be located upstream or downstream from the coding sequence and affect transcription of the sequence.

In certain embodiments, it is preferred that the flanking sequence is a transcriptional regulatory region that drives high-level gene expression in the target cell. The transcriptional regulatory region may comprise, for example, a promoter, enhancer, silencer, repressor element, or combinations thereof. The transcriptional regulatory region may be either constitutive, tissue-specific, cell-type specific (i.e., the region is drives higher levels of transcription in a one type of tissue or cell as compared to another), or regulatable (i.e., responsive to interaction with a compound). The source of a transcriptional regulatory region may be any prokaryotic or eukaryotic organism, any vertebrate or invertebrate organism, or any plant, provided that the flanking sequence functions in a cell by causing transcription of a nucleic acid within that cell. A wide variety of transcriptional regulatory regions may be utilized in practicing the present invention.

Suitable transcriptional regulatory regions include, for example, the CMV promoter (i.e., the CMV-immediate early promoter); promoters from eukaryotic genes (i.e., the estrogen-inducible chicken ovalbumin gene, the interferon genes, the gluco-corticoid-inducible tyrosine aminotransferase gene, and the thymidine kinase gene); and the major early and late adenovirus gene promoters; the SV40 early promoter region (Bernoist and Chambon, 1981, *Nature* 290:304-10); the promoter contained in the 3' long terminal repeat (LTR) of Rous sarcoma virus (RSV) (Yamamoto, et al., 1980, *Cell* 22:787-97); the herpes simplex virus thymidine kinase (HSV-TK) promoter (Wagner et al., 1981, *Proc. Natl. Acad. Sci. U.S.A.* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Tissue- and/or cell-type specific transcriptional control regions include, for example, the elastase I gene control region which is active in pancreatic acinar cells (Swift et al., 1984, *Cell* 38:639-46; Ornitz et al., 1986, *Cold Spring Harbor Symp. Quant. Biol.*

50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region in testicular, breast, lymphoid and mast cells (Leder et al., 1986, *Cell* 45:485-95); the albumin gene control region in liver (Pinkert et al., 1987, *Genes and Devel.* 1:268-76); the alpha-feto-protein gene control region in liver (Krumlauf et al., 1985, *Mol. Cell. Biol.*, 5:1639-48; Hammer et al., 1987, *Science* 235:53-58); the alpha 1-antitrypsin gene control region in liver (Kelsey et al., 1987, *Genes and Devel.* 1:161-71); the beta-globin gene control region in myeloid cells (Mogram et al., 1985, *Nature* 315:338-40; Kollias et al., 1986, *Cell* 46:89-94); the myelin basic protein gene control region in oligodendrocyte cells in the brain (Readhead et al., 1987, *Cell* 48:703-12); the myosin light chain-2 gene control region in skeletal muscle (Sani, 1985, *Nature* 314:283-86); the gonadotropic releasing hormone gene control region in the hypothalamus (Mason et al., 1986, *Science* 234:1372-78), and the tyrosinase promoter in melanoma cells (Hart, I. Semin Oncol 1996 February; 23(1):154-8; Siders, et al. Cancer Gene Tier 1998 September-October; 5(5):281-91), among others. Inducible promoters that are activated in the presence of a certain compound or condition such as light, heat, radiation, tetracycline, or heat shock proteins, for example, may also be utilized (see, for example, WO 00/10612). Other suitable promoters are known in the art.

As described above, enhancers may also be suitable flanking sequences. Enhancers are cis-acting elements of DNA, usually about 10-300 bp in length, that act on the promoter to increase transcription. Enhancers are typically orientation- and position-independent, having been identified both 5' and 3' to controlled coding sequences. Several enhancer sequences available from mammalian genes are known (i.e., globin, elastase, albumin, alpha-feto-protein and insulin). Similarly, the SV40 enhancer, the cytomegalovirus early promoter enhancer, the polyoma enhancer, and adenovirus enhancers are useful with eukaryotic promoter sequences. While an enhancer may be spliced into the vector at a position 5' or 3' to nucleic acid coding sequence, it is typically located at a site 5' from the promoter. Other suitable enhancers are known in the art, and would be applicable to the present invention.

While preparing reagents of the present invention, cells may need to be transfected or transformed. Transfection refers to the uptake of foreign or exogenous DNA by a tell, and a cell has been transfected when the exogenous DNA has been introduced inside the cell membrane. A number of transfection techniques are well known in the art (i.e., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197). Such techniques can be used to introduce one or more exogenous DNA moieties into suitable host cells.

In certain embodiments, it is preferred that transfection of a cell results in transformation of that cell. A cell is transformed when there is a change in a characteristic of the cell, being transformed when it has been modified to contain a new nucleic acid. Following transfection, the transfected nucleic acid may recombine with that of the cell by physically integrating into a chromosome of the cell, may be maintained transiently as an episomal element without being replicated, or may replicate independently as a plasmid. A cell is stably transformed when the nucleic acid is replicated with the division of the cell.

The present invention further provides isolated immunogenic targets in polypeptide form. A polypeptide is considered isolated where it: (1) has been separated from at least about 50 percent of polynucleotides, lipids, carbohydrates, or other materials with which it is naturally found when isolated from the source cell; (2) is not linked (by covalent or noncovalent interaction) to all or a portion of a polypeptide to which the "isolated polypeptide" is linked in nature; (3) is operably linked (by covalent or noncovalent interaction) to a polypeptide with which it is not linked in nature; or, (4) does not occur in nature. Preferably, the isolated polypeptide is substantially free from any other contaminating polypeptides or other contaminants that are found in its natural environment that would interfere with its therapeutic, diagnostic, prophylactic or research use.

Immunogenic target polypeptides may be mature polypeptides, as defined herein, and may or may not have an amino terminal methionine residue, depending on the method by which they are prepared. Further contemplated are related polypeptides such as, for example, fragments, variants (i.e., allelic, splice), orthologs, homologues, and derivatives, for example, that possess at least one characteristic or activity (i.e., activity, antigenicity) of the immunogenic target. Also related are peptides, which refers to a series of contiguous amino acid residues having a sequence corresponding to at least a portion of the polypeptide from which its sequence is derived. In preferred embodiments, the peptide comprises about 5-10 amino acids, 10-15 amino acids, 15-20 amino acids, 20-30 amino acids, or 30-50 amino acids. In a more preferred embodiment, a peptide comprises 9-12 amino acids, suitable for presentation upon Class I MHC molecules, for example.

A fragment of a nucleic acid or polypeptide comprises a truncation of the sequence (i.e., nucleic acid or polypeptide) at the amino terminus (with or without a leader sequence) and/or the carboxy terminus. Fragments may also include variants (i.e., allelic, splice), orthologs, homologues, and other variants having one or more amino acid additions or substitutions or internal deletions as compared to the parental sequence. In preferred embodiments, truncations and/or deletions comprise about 10 amino acids, 20 amino acids, 30 amino acids, 40 amino acids, 50 amino acids, or more. The polypeptide fragments so produced will comprise about 10 amino acids, 25 amino acids, 30 amino acids, 40 amino acids, 50 amino acids, 60 amino acids, 70 amino acids, or more. Such polypeptide fragments may optionally comprise an amino terminal methionine residue. It will be appreciated that such fragments can be used, for example, to generate antibodies or cellular immune responses to immunogenic target polypeptides.

A variant is a sequence having one or more sequence substitutions, deletions, and/or additions as compared to the subject sequence. Variants may be naturally occurring or artificially constructed. Such variants may be prepared from the corresponding nucleic acid molecules. In preferred embodiments, the variants have from 1 to 3, or from 1 to 5, or from 1 to 10, or from 1 to 15, or from 1 to 20, or from 1 to 25, or from 1 to 30, or from 1 to 40, or from 1 to 50, or more than 50 amino acid substitutions, insertions, additions and/or deletions.

An allelic variant is one of several possible naturally-occurring alternate forms of a gene occupying a given locus on a chromosome of an organism or a population of organisms. A splice variant is a polypeptide generated from one of several RNA transcript resulting from splicing of a primary transcript. An ortholog is a similar nucleic acid or polypeptide sequence from another species. For example, the mouse and human versions of an immunogenic target polypeptide may be considered orthologs of each other. A derivative of a sequence is one that is derived from a parental sequence those sequences having substitutions, additions, deletions, or chemically modified variants. Variants may also include fusion proteins, which refers to the fusion of one or more first sequences (such as a peptide) at the amino or carboxy terminus of at least one other sequence (such as a heterologous peptide).

"Similarity" is a concept related to identity, except that similarity refers to a measure of relatedness which includes both identical matches and conservative substitution matches. If two polypeptide sequences have, for example, $10/20$ identical amino acids, and the remainder are all non-conservative substitutions, then the percent identity and similarity would both be 50%. If in the same example, there are five more positions where there are conservative substitutions, then the percent identity remains 50%, but the percent similarity would be 75% ($15/20$). Therefore, in cases where there are conservative substitutions, the percent similarity between two polypeptides will be higher than the percent identity between those two polypeptides.

Substitutions may be conservative, or non-conservative, or any combination thereof. Conservative amino acid modifications to the sequence of a polypeptide (and the corresponding modifications to the encoding nucleotides) may produce polypeptides having functional and chemical characteristics similar to those of a parental polypeptide. For example, a "conservative amino acid substitution" may involve a substitution of a native amino acid residue with a non-native residue such that there is little or no effect on the size, polarity, charge, hydrophobicity, or hydrophilicity of the amino acid residue at that position and, in particular, does not result in decreased immunogenicity. Suitable conservative amino acid substitutions are shown in Table I.

TABLE I

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of polypeptide using well-known techniques. For identifying suitable areas of the molecule that may be changed without destroying biological activity (i.e., MHC binding, immunogenicity), one skilled in the art may target areas not believed to be important for that activity. For example, when similar polypeptides with similar activities from the same species or from other species are known, one skilled in the art may compare the amino acid sequence of a polypeptide to such similar polypeptides. By performing such analyses, one can identify residues and portions of the molecules that are conserved among similar polypeptides. It will be appreciated that changes in areas of the molecule that are not conserved relative to such similar polypeptides would be less likely to adversely affect the biological activity and/or structure of a polypeptide. Similarly, the residues required for binding to MHC are known, and may be modified to improve binding. However, modifications resulting in decreased binding to MHC will not be appropriate in most situations. One skilled in the art would also know that, even in relatively conserved regions, one may substitute chemically similar amino acids for the naturally occurring residues while retaining activity. Therefore, even areas that may be important for biological activity or for structure may be subject to conservative amino acid substitutions without destroying the biological activity or without adversely affecting the polypeptide structure.

Other preferred polypeptide variants include glycosylation variants wherein the number and/or type of glycosylation sites have been altered compared to the subject amino acid sequence. In one embodiment, polypeptide variants comprise a greater or a lesser number of N-linked glycosylation sites than the subject amino acid sequence. An N-linked glycosylation site is characterized by the sequence Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. To affect O-linked glycosylation of a polypeptide, one would modify serine and/or threonine residues.

Additional preferred variants include cysteine variants, wherein one or more cysteine residues are deleted or substituted with another amino acid (e.g., serine) as compared to the subject amino acid sequence set. Cysteine variants are useful when polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, the isolated polypeptides of the current invention include fusion polypeptide segments that assist in purification of the polypeptides. Fusions can be made either at the amino terminus or at the carboxy terminus of the subject polypeptide variant thereof. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein. Suitable fusion segments include, among others, metal binding domains (e.g., a poly-histidine segment), immunoglobulin binding domains (i.e., Protein A, Protein G, T cell, B cell, Fc receptor, or complement protein antibody-binding domains), sugar binding domains (e.g., a maltose binding domain), and/or a "tag" domain (i.e., at least a portion of α-galactosidase, a strep tag peptide, a T7 tag peptide, a FLAG peptide, or other domains that can be purified using compounds that bind to the domain, such as monoclonal antibodies). This tag is typically fused to the polypeptide upon expression of the polypeptide, and can serve as a means for affinity purification of the sequence of interest polypeptide from the host cell. Affinity purification can be accomplished, for example, by column chromatography using antibodies against the tag as an affinity matrix. Optionally, the tag can subsequently be removed from the purified sequence of interest polypeptide by various means such as using certain peptidases for cleavage. As described below, fusions may also be made between a TA and a co-stimulatory components such as the chemokines CXC10 (IP-10), CCL7 (MCP-3), or CCL5 (RANTES), for example.

A fusion motif may enhance transport of an immunogenic target to an MHC processing compartment, such as the endoplasmic reticulum. These sequences, referred to as tranduction or transcytosis sequences, include sequences derived from HIV tat (see Kim et al. 1997 J. Immunol. 159:1666), Drosophila antennapedia (see Schutze-Redelmeier et al. 1996 J. Immunol. 157:650), or human period-1 protein (hPER1; in particular, SRRHHCRSKAKRSRHH (SEQ ID NO: 105).

In addition, the polypeptide or variant thereof may be fused to a homologous polypeptide to form a homodimer or to a heterologous polypeptide to form a heterodimer. Heterologous peptides and polypeptides include, but are not limited to: an epitope to allow for the detection and/or isolation of a fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide or variant thereof.

In certain embodiments, it may be advantageous to combine a nucleic acid sequence encoding an immunogenic target, polypeptide, or derivative thereof with one or more nucleic acid sequences encoding one or more co-stimulatory component(s) such as cell surface proteins, cytokines or chemokines in a composition of the present invention. The co-stimulatory component may be included in the composition as a polypeptide or as a nucleic acid encoding the polypeptide, for example. Suitable co-stimulatory molecules include, for instance, polypeptides that bind members of the CD28 family (i.e., CD28, ICOS; Hutloff, et al. *Nature* 1999, 397: 263-265; Peach, et al. *J Exp Med* 1994, 180: 2049-2058) such as the CD28 binding polypeptides B7.1 (CD80; Schwartz, 1992; Chen et al, 1992; Ellis, et al. *J. Immunol.*, 156(8): 2700-9) and B7.2 (CD86; Ellis, et al. *J Immunol.*, 156(8): 2700-9); mutated and derivative B7 molecules (WO 00/66162); polypeptides which bind members of the integrin family (i.e., LFA-1 (CD11a/CD18); Sedwick, et al. *J Immunol* 1999, 162: 1367-1375; Wülfing, et al. *Science* 1998, 282: 2266-2269; Lub, et al. *Immunol Today* 1995, 16: 479-483) including members of the ICAM family (i.e., ICAM-1, -2 or -3); polypeptides which bind CD2 family members (i.e., CD2, signalling lymphocyte activation molecule (CDw150 or "SLAM"; Aversa, et al. *J Immunol* 1997, 158: 4036-4044)) such as CD58 (LFA-3; CD2 ligand; Davis, et al. *Immunol Today* 1996, 17: 177-187) or SLAM ligands (Sayos, et al. *Nature* 1998, 395: 462-469); polypeptides which bind heat stable antigen (HSA or CD24; Zhou, et al. *Eur J Immunol* 1997, 27: 2524-2528); polypeptides which bind to members of the TNF receptor (TNFR) family (i.e., 4-1BB (CD137; Vinay, et al. *Semin Immunol* 1998, 10: 481-489), OX40 (CD134; Weinberg, et al. *Semin Immunol* 1998, 10: 471-480; Higgins, et al. *J Immunol* 1999, 162: 486-493), and CD27 (Lens, et al. *Semin Immunol* 1998, 10: 491-499)) such as 4-1BBL (4-1BB ligand; Vinay, et al. *Semin Immunol* 1998, 10: 481-48; DeBenedette, et al. *J Immunol* 1997, 158: 551-559), TNFR associated factor-1 (TRAF-1; 4-1BB ligand; Saoulli, et al. *J Exp Med* 1998, 187: 1849-1862, Arch, et al. *Mol Cell Biol* 1998, 18: 558-565), TRAF-2 (4-1BB and OX40 ligand; Saoulli, et al. *J Exp Med* 1998, 187: 1849-1862; Oshima, et al. *Int Immunol* 1998, 10: 517-526, Kawamata, et al. *J Biol Chem* 1998, 273: 5808-5814), TRAF-3 (4-1BB and OX40 ligand; Arch, et al. *Mol Cell Biol* 1998, 18: 558-565; Jang, et al. *Biochem Biophys Res Commun* 1998, 242: 613-620; Kawamata S, et al. *J Biol Chem* 1998, 273: 5808-5814), OX40L (OX40 ligand; Gramaglia, et al. *J Immunol* 1998, 161: 6510-6517), TRAF-5 (OX40 ligand; Arch, et al. *Mol Cell Biol* 1998, 18: 558-565; Kawamata, et al. *J Biol Chem* 1998, 273: 5808-5814), and CD70 (CD27 ligand; Couderc, et al. *Cancer Gene Ther.*, 5(3): 163-75). CD154 (CD40 ligand or "CD40L"; Gurunathan, et al. *J Immunol.*, 1998, 161: 4563-4571; Sine, et al. *Hum. Gene Ther.*, 2001, 12: 1091-1102) may also be suitable.

One or more cytokines may also be suitable co-stimulatory components or "adjuvants", either as polypeptides or being encoded by nucleic acids contained within the compositions of the present invention (Parmiani, et al. Immunol Lett 2000 Sep. 15; 74(1): 41-4; Berzofsky, et al. Nature Immunol. 1: 209-219). Suitable cytokines include, for example, interleukin-2 (IL-2) (Rosenberg, et al. *Nature Med.* 4: 321-327 (1998)), IL-4, IL-7, IL-12 (reviewed by Pardoll, 1992; Harries, et al. J. Gene Med. 2000 July-August; 2(4):243-9; Rao, et al. *J. Immunol.* 156: 3357-3365 (1996)), IL-15 (Xin, et al. *Vaccine*, 17:858-866, 1999), IL-16 (Cruikshank, et al. J. Leuk Biol. 67(6): 757-66, 2000), IL-18 (*J. Cancer Res. Clin. Oncol.* 2001. 127(12): 718-726), GM-CSF (CSF (Disis, et al. *Blood*, 88: 202-210 (1996)), tumor necrosis factor-alpha (TNF-α), or interferons such as IFN-α or INF-γ. Other cytokines may also be suitable for practicing the present invention, as is known in the art.

Chemokines may also be utilized. For example, fusion proteins comprising CXCL10 (IP-10) and CCL7 (MCP-3) fused to a tumor self-antigen have been shown to induce anti-tumor immunity (Biragyn, et al. *Nature Biotech.* 1999, 17: 253-258). The chemokines CCL3 (MIP-1α) and CCL5 (RANTES) (Boyer, et al. *Vaccine*, 1999, 17 (Supp. 2): S53-S64) may also be of use in practicing the present invention. Other suitable chemokines are known in the art.

It is also known in the art that suppressive or negative regulatory immune mechanisms may be blocked, resulting in enhanced immune responses. For instance, treatment with anti-CTLA-4 (Shrikant, et al. *Immunity*, 1996, 14: 145-155; Sutmuller, et al. *J. Exp. Med.*, 2001, 194: 823-832), anti-CD25 (Sutmuller, supra), anti-CD4 (Matsui, et al. *J. Immunol.*, 1999, 163: 184-193), the fusion protein IL13Ra2-Fc (Terabe, et al. *Nature Immunol.*, 2000, 1: 515-520), and combinations thereof (i.e., anti-CTLA-4 and anti-CD25, Sutmuller, supra) have been shown to upregulate anti-tumor immune responses and would be suitable in practicing the present invention.

Any of these components may be used alone or in combination with other agents. For instance, it has been shown that a combination of CD80, ICAM-1 and LFA-3 ("TRICOM") may potentiate anti-cancer immune responses (Hodge, et al. *Cancer Res.* 59: 5800-5807 (1999). Other effective combinations include, for example, IL-12+GM-CSF (Ahlers, et al. *J. Immunol.*, 158: 3947-3958 (1997); Iwasaki, et al. *J. Immunol.* 158: 4591-4601 (1997)), IL-12+GM-CSF+TNF-α (Ahlers, et al. *Int. Immunol.* 13: 897-908 (2001)), CD80+IL-12 (Fruend, et al. *Int. J. Cancer,* 85: 508-517 (2000); Rao, et al. supra), and CD86+GM-CSF+IL-12 (Iwasaki, supra). One of skill in the art would be aware of additional combinations useful in carrying out the present invention. In addition, the skilled artisan would be aware of additional reagents or methods that may be used to modulate such mechanisms. These reagents and methods, as well as others known by those of skill in the art, may be utilized in practicing the present invention.

Additional strategies for improving the efficiency of nucleic acid-based immunization may also be used including, for example, the use of self-replicating viral replicons (Caley, et al. 1999. *Vaccine,* 17: 3124-2135; Dubensky, et al. 2000. *Mol. Med.* 6: 723-732; Leitner, et al. 2000. *Cancer Res.* 60: 51-55), codon optimization (Liu, et al. 2000. *Mol. Ther.,* 1: 497-500; Dubensky, supra; Huang, et al. 2001. *J. Virol.* 75: 4947-4951), in vivo electroporation (Widera, et al. 2000. *J. Immunol.* 164: 4635-3640), incorporation of CpG stimulatory motifs (Gurunathan, et al. *Ann. Rev. Immunol.,* 2000, 18: 927-974; Leitner, supra; Cho, et al. J. Immunol. 168(10): 4907-13), sequences for targeting of the endocytic or ubiquitin-processing pathways (Thomson, et al. 1998. *J. Virol.* 72: 2246-2252; Velders, et al. 2001. *J. Immunol.* 166: 5366-5373), Marek's disease virus type 1 VP22 sequences (J. Virol. 76(6):2676-82, 2002), prime-boost regimens (Gurunathan, supra; Sullivan, et al. 2000. *Nature,* 408: 605-609; Hanke, et al. 1998. *Vaccine,* 16: 439-445; Amara, et al. 2001. *Science,* 292: 69-74), and the use of mucosal delivery vectors such as Salmonella (Darji, et al. 1997. *Cell,* 91: 765-775; Woo, et al. 2001. *Vaccine,* 19: 2945-2954). Other methods are known in the art, some of which are described below.

Chemotherapeutic agents, radiation, anti-angiogenic compounds, or other agents may also be utilized in treating and/or preventing cancer using immunogenic targets (Sebti, et al. Oncogene 2000 Dec. 27; 19(56):6566-73). For example, in treating metastatic breast cancer, useful chemotherapeutic agents include cyclophosphamide, doxorubicin, paclitaxel, docetaxel, navelbine, capecitabine, and mitomycin C, among others. Combination chemotherapeutic regimens have also proven effective including cyclophosphamide+methotrexate+5-fluorouracil; cyclophosphamide+doxorubicin+5-fluorouracil; or, cyclophosphamide+doxorubicin, for example. Other compounds such as prednisone, a taxane, navelbine, mitomycin C, or vinblastine have been utilized for various reasons. A majority of breast cancer patients have estrogen-receptor positive (ER+) tumors and in these patients, endocrine therapy (i.e., tamoxifen) is preferred over chemotherapy. For such patients, tamoxifen or, as a second line therapy, progestins (medroxyprogesterone acetate or megestrol acetate) are preferred. Aromatase inhibitors (i.e., aminoglutethimide and analogs thereof such as letrozole) decrease the availability of estrogen needed to maintain tumor growth and may be used as second or third line endocrine therapy in certain patients.

Other cancers may require different chemotherapeutic regimens. For example, metastatic colorectal cancer is typically treated with Camptosar (irinotecan or CPT-11), 5-fluorouracil or leucovorin, alone or in combination with one another. Proteinase and integrin inhibitors such as as the MMP inhibitors marimastate (British Biotech), COL-3 (Collagenex), Neovastat (Aeterna), AG3340 (Agouron), BMS-275291 (Bristol Myers Squibb), CGS 27023A (Novartis) or the integrin inhibitors Vitaxin (Medimmune), or MED1522 (Merck KgaA) may also be suitable for use. As such, immunological targeting of immunogenic targets associated with colorectal cancer could be performed in combination with a treatment using those chemotherapeutic agents. Similarly, chemotherapeutic agents used to treat other types of cancers are well-known in the art and may be combined with the immunogenic targets described herein.

Many anti-angiogenic agents are known in the art and would be suitable for co-administration with the immunogenic target vaccines (see, for example, Timar, et al. 2001. *Pathology Oncol. Res.,* 7(2): 85-94). Such agents include, for example, physiological agents such as growth factors (i.e., ANG-2, NK1, 2, 4 (HGF), transforming growth factor beta (TGF-β)), cytokines (i.e., interferons such as IFN-α, -β, -γ, platelet factor 4 (PF-4), PR-39), proteases (i.e., cleaved AT-III, collagen XVIII fragment (Endostatin)), HmwKallikrein-d5 plasmin fragment (Angiostatin), prothrombin-F1-2, TSP-1), protease inhibitors (i.e., tissue inhibitor of metalloproteases such as TIMP-1, -2, or -3; maspin; plasminogen activator-inhibitors such as PAI-1; pigment epithelium derived factor (PEDF)), Tumstatin (available through ILEX, Inc.), antibody products (i.e., the collagen-binding antibodies HUIV26, HUI77, XL313; anti-VEGF; anti-integrin (i.e., Vitaxin, (Lxsys))), and glycosidases (i.e., heparinase-I, -III). "Chemical" or modified physiological agents known or believed to have anti-angiogenic potential include, for example, vinblastine, taxol, ketoconazole, thalidomide, dolestatin, combrestatin A, rapamycin (Guba, et al. 2002, *Nature Med.,* 8: 128-135), CEP-7055 (available from Cephalon, Inc.), flavone acetic acid, Bay 12-9566 (Bayer Corp.), AG3340 (Agouron, Inc.), CGS 27023A (Novartis), tetracylcine derivatives (i.e., COL-3 (Collagenix, Inc.)), Neovastat (Aeterna), BMS-275291 (Bristol-Myers Squibb), low dose 5-FU, low dose methotrexate (MTX), irsofladine, radicicol, cyclosporine, captopril, celecoxib, D45152-sulphated polysaccharide, cationic protein (Protamine), cationic peptide-VEGF, Suramin (polysulphonated napthyl urea), compounds that interfere with the function or production of VEGF (i.e., SU5416 or SU6668 (Sugen), PTK787/ZK22584 (Novartis)), Distamycin A, Angiozyme (ribozyme), isoflavinoids, staurosporine derivatives, genistein, EMD121974 (Merck KcgaA), tyrphostins, isoquinolones, retinoic acid, carboxyamidotriazole, TNP-470, octreotide, 2-methoxyestradiol, aminosterols (i.e., squalamine), glutathione analogues (i.e., N-acetyl-L-cysteine), combretastatin A4 (Oxigene), Eph receptor blocking agents (*Nature,* 414:933-938, 2001), Rh-Angiostatin, Rh-Endostatin (WO 01/93897), cyclic-RGD peptide, accutin-disintegrin, benzodiazepenes, humanized anti-avb3 Ab, Rh-PAI-2, amiloride, p-amidobenzamidine, anti-uPA ab, anti-uPAR Ab, L-phanylalanin-N-methylamides (i.e., Batimistat, Marimastat), AG3340, and minocycline. Many other suitable agents are known in the art and would suffice in practicing the present invention.

The present invention may also be utilized in combination with "non-traditional" methods of treating cancer. For example, it has recently been demonstrated that administration of certain anaerobic bacteria may assist in slowing tumor growth. In one study, *Clostridium novyi* was modified to eliminate a toxin gene carried on a phage episome and administered to mice with colorectal tumors (Dang, et al. *P.N.A.S. USA,* 98(26): 15155-15160, 2001). In combination with chemotherapy, the treatment was shown to cause tumor necrosis in the animals. The reagents and methodologies described in this application may be combined with such treatment methodologies.

Nucleic acids encoding immunogenic targets may be administered to patients by any of several available techniques. Various viral vectors that have been successfully utilized for introducing a nucleic acid to a host include retrovirus, adenovirus, adeno-associated virus (AAV), herpes virus, and poxvirus, among others. It is understood in the art that many such viral vectors are available in the art. The vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.).

Preferred retroviral vectors are derivatives of lentivirus as well as derivatives of murine or avian retroviruses. Examples of suitable retroviral vectors include, for example, Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of retroviral vectors can incorporate multiple exogenous nucleic acid sequences. As recombinant retroviruses are defective, they require assistance in order to produce infectious vector particles. This assistance can be provided by, for example, helper cell lines encoding retrovirus structural genes. Suitable helper cell lines include Ψ2, PA317 and PA12, among others. The vector virions produced using such cell lines may then be used to infect a tissue cell line, such as NIH 3T3 cells, to produce large quantities of chimeric retroviral virions. Retroviral vectors may be administered by traditional methods (i.e., injection) or by implantation of a "producer cell line" in proximity to the target cell population (Culver, K., et al., 1994, *Hum. Gene Ther.*, 5 (3): 343-79; Culver, K., et al., *Cold Spring Harb. Symp. Quant. Biol.*, 59: 685-90); Oldfield, E., 1993, *Hum. Gene Ther.*, 4 (1): 39-69). The producer cell line is engineered to produce a viral vector and releases viral particles in the vicinity of the target cell. A portion of the released viral particles contact the target cells and infect those cells, thus delivering a nucleic acid of the present invention to the target cell. Following infection of the target cell, expression of the nucleic acid of the vector occurs.

Adenoviral vectors have proven especially useful for gene transfer into eukaryotic cells (Rosenfeld, M., et al., 1991, *Science*, 252 (5004): 431-4; Crystal, R., et al., 1994, *Nat. Genet.*, 8 (1): 42-51), the study eukaryotic gene expression (Levrero, M., et al., 1991, *Gene*, 101 (2): 195-202), vaccine development (Graham, F. and Prevec, L., 1992, *Biotechnology*, 20: 363-90), and in animal models (Stratford-Perricaudet, L., et al., 1992, *Bone Marrow Transplant.*, 9 (Suppl. 1): 151-2; Rich, D., et al., 1993, *Hum. Gene Ther.*, 4 (4): 461-76). Experimental routes for administrating recombinant Ad to different tissues in vivo have included intratracheal instillation (Rosenfeld, M., et al., 1992, *Cell*, 68 (1): 143-55) injection into muscle (Quantin, B., et al., 1992, *Proc. Natl. Acad. Sci. U.S.A.*, 89 (7): 2581-4), peripheral intravenous injection (Herz, J., and Gerard, R., 1993, *Proc. Natl. Acad. Sci. U.S.A.*, 90 (7): 2812-6) and stereotactic inoculation to brain (Le Gal La Salle, G., et al., 1993, *Science*, 259 (5097): 988-90), among others.

Adeno-associated virus (AAV) demonstrates high-level infectivity, broad host range and specificity in integrating into the host cell genome (Hermonat, P., et al., 1984, *Proc. Natl. Acad. Sci. U.S.A.*, 81 (20): 6466-70). And Herpes Simplex Virus type-1 (HSV-1) is yet another attractive vector system, especially for use in the nervous system because of its neurotropic property (Geller, A., et al., 1991, *Trends Neurosci.*, 14 (10): 428-32; Glorioso, et al., 1995, *Mol. Biotechnol.*, 4 (1): 87-99; Glorioso, et al., 1995, *Annu. Rev. Microbiol.*, 49: 675-710).

Poxvirus is another useful expression vector (Smith, et al. 1983, *Gene*, 25 (1): 21-8; Moss, et al, 1992, *Biotechnology*, 20: 345-62; Moss, et al, 1992, *Curr. Top. Microbiol. Immunol.*, 158: 25-38; Moss, et al. 1991. *Science*, 252: 1662-1667). Poxviruses shown to be useful include vaccinia, NYVAC, avipox, fowlpox, canarypox, ALVAC, and ALVAC (2), among others.

NYVAC (vP866) was derived from the Copenhagen vaccine strain of vaccinia virus by deleting six nonessential regions of the genome encoding known or potential virulence factors (see, for example, U.S. Pat. Nos. 5,364,773 and 5,494, 807). The deletion loci were also engineered as recipient loci for the insertion of foreign genes. The deleted regions are: thymidine kinase gene (TK; J2R); hemorrhagic region (u; B13R+B14R); A type inclusion body region (ATI; A26L); hemagglutinin gene (HA; A56R); host range gene region (C7L-K1L); and, large subunit, ribonucleotide reductase (I4L). NYVAC is a genetically engineered vaccinia virus strain that was generated by the specific deletion of eighteen open reading frames encoding gene products associated with virulence and host range. NYVAC has been show to be useful for expressing TAs (see, for example, U.S. Pat. No. 6,265, 189). NYVAC (vP866), vP994, vCP205, vCP1433, placZH6H4Lreverse, pMPC6H6K3E3 and pC3H6FHVB were also deposited with the ATCC under the terms of the Budapest Treaty, accession numbers VR-2559, VR-2558, VR-2557, VR-2556, ATCC-97913, ATCC-97912, and ATCC-97914, respectively.

ALVAC-based recombinant viruses (i.e., ALVAC-1 and ALVAC-2) are also suitable for use in practicing the present invention (see, for example, U.S. Pat. No. 5,756,103). ALVAC (2) is identical to ALVAC (1) except that ALVAC (2) genome comprises the vaccinia E3L and K3L genes under the control of vaccinia promoters (U.S. Pat. No. 6,130,066; Beattie et al., 1995a, 1995b, 1991; Chang et al., 1992; Davies et al., 1993). Both ALVAC (1) and ALVAC (2) have been demonstrated to be useful in expressing foreign DNA sequences, such as TAs (Tartaglia et al., 1993 a,b; U.S. Pat. No. 5,833, 975). ALVAC was deposited under the terms of the Budapest Treaty with the American Type Culture Collection (ATCC), 10801 University Boulevard, Manassas, Va. 20110-2209, USA, ATCC accession number VR-2547.

Another useful poxvirus vector is TROVAC. TROVAC refers to an attenuated fowlpox that was a plaque-cloned isolate derived from the FP-1 vaccine strain of fowlpoxvirus which is licensed for vaccination of 1 day old chicks. TROVAC was likewise deposited under the terms of the Budapest Treaty with the ATCC, accession number 2553.

"Non-viral" plasmid vectors may also be suitable in practicing the present invention. Preferred plasmid vectors are compatible with bacterial, insect, and/or mammalian host cells. Such vectors include, for example, PCR-II, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT pub. No. WO 90/14363) and pFastBacDual (Gibco-BRL, Grand Island, N.Y.) as well as Bluescript® plasmid derivatives (a high copy number COLE1-based phagemid, Stratagene Cloning Systems, La Jolla, Calif.), PCR cloning plasmids designed for cloning Taq-amplified PCR products (e.g., TOPO™ TA Cloning® kit, PCR2.1® plasmid derivatives, Invitrogen, Carlsbad, Calif.). Bacterial vectors may also be used with the current invention. These vectors include, for example, *Shigella, Salmonella, Vibrio cholerae, Lactobacillus, Bacille calmette guérin* (BCG), and *Streptococcus* (see for example, WO 88/6626; WO 90/0594; WO 91/13157; WO 92/1796; and WO 92/21376). Many other non-viral plasmid expression vectors and systems are known in the art and could be used with the current invention.

Suitable nucleic acid delivery techniques include DNA-ligand complexes, adenovirus-ligand-DNA complexes, direct injection of DNA, $CaPO_4$ precipitation, gene gun techniques, electroporation, and colloidal dispersion systems, among others. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, *Trends Biochem. Sci.*, 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

An immunogenic target may also be administered in combination with one or more adjuvants to boost the immune response. Exemplary adjuvants are shown in Table II below:

The immunogenic targets of the present invention may also be used to generate antibodies for use in screening assays or for immunotherapy, which are another aspect of the present invention. Other uses would be apparent to one of skill in the art. The term "antibody" includes antibody fragments, as are known in the art, including Fab, $Fab_2$, single chain antibodies (Fv for example), humanized antibodies, chimeric antibodies, human antibodies, produced by several methods as are known in the art.

Methods of preparing and utilizing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al. *Using Antibodies: A Laboratory Manual, Portable Protocol No. 1*, 1998; Kohler and Milstein, Nature, 256:495 (1975)); Jones et al. Nature, 321:522-525 (1986); Riechmann et al. Nature, 332:323-329 (1988); Presta (Curr. Op. Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boerner et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; and, 5,661,016). The antibodies or derivatives therefrom may also be conjugated to therapeutic moieties such as cytotoxic drugs or toxins, or active fragments thereof such as diptheria A chain, exotoxin A chain, ricin A chain, abrin A chain, curcin, crotin, phenomycin,

TABLE II

Types of Immunologic Adjuvants

| Type of Adjuvant | General Examples | Specific Examples/References |
|---|---|---|
| Gel-type | Aluminum hydroxide/phosphate ("alum adjuvants") | (Aggerbeck and Heron, 1995) |
|  | Calcium phosphate | (Relyveld, 1986) |
| Microbial | Muramyl dipeptide (MDP) | (Chedid et al., 1986) |
|  | Bacterial exotoxins | Cholera toxin (CT), *E. coli* labile toxin (LT)(Freytag and Clements, 1999) |
|  | Endotoxin-based adjuvants | Monophosphoryl lipid A (MPL) (Ulrich and Myers, 1995) |
|  | Other bacterial | CpG oligonucleotides (Corral and Petray, 2000), BCG sequences (Krieg, et al. Nature, 374:576), tetanus toxoid (Rice, et al. J. Immunol., 2001, 167: 1558-1565) |
| Particulate | Biodegradable Polymer microspheres | (Gupta et al., 1998) |
|  | Immunostimulatory complexes (ISCOMs) | (Morein and Bengtsson, 1999) |
|  | Liposomes | (Wassef et al., 1994) |
| Oil-emulsion and surfactant-based adjuvants | Freund's incomplete adjuvant | (Jensen et al., 1998) |
|  | Microfluidized emulsions | MF59 (Ott et al., 1995) |
|  |  | SAF (Allison and Byars, 1992) |
|  |  | (Allison, 1999) |
|  | Saponins | QS-21 (Kensil, 1996) |
| Synthetic | Muramyl peptide derivatives | Murabutide (Lederer, 1986) |
|  |  | Threony-MDP (Allison, 1997) |
|  | Nonionic block copolymers | L121 (Allison, 1999) |
|  | Polyphosphazene (PCPP) | (Payne et al., 1995) |
|  | Synthetic polynucleotides | Poly A:U, Poly I:C (Johnson, 1994) |
|  | Thalidomide derivatives | CC-4047/ACTIMID (J. Immunol., 168(10):4914-9) | enomycin, among others. Cytotoxic agents may also include radiochemicals. Antibodies and their derivatives may be incorporated into compositions of the invention for use in vitro or in vivo.

Nucleic acids, proteins, or derivatives thereof representing an immunogenic target may be used in assays to determine the presence of a disease state in a patient, to predict prognosis, or to determine the effectiveness of a chemotherapeutic or other treatment regimen. Expression profiles, performed as is known in the art, may be used to determine the relative level of expression of the immunogenic target. The level of expression may then be correlated with base levels to determine whether a particular disease is present within the patient, the patient's prognosis, or whether a particular treatment regimen is effective. For example, if the patient is being treated with a particular chemotherapeutic regimen, a decreased level of expression of an immunogenic target in the patient's tissues (i.e., in peripheral blood) may indicate the regimen is decreasing the cancer load in that host. Similarly, if the level of expression is increasing, another therapeutic modality may need to be utilized. In one embodiment, nucleic acid probes corresponding to a nucleic acid encoding an immunogenic target may be attached to a biochip, as is known in the art, for the detection and quantification of expression in the host.

It is also possible to use nucleic acids, proteins, derivatives therefrom, or antibodies thereto as reagents in drug screening assays. The reagents may be used to ascertain the effect of a drug candidate on the expression of the immunogenic target in a cell line, or a cell or tissue of a patient. The expression profiling technique may be combined with high throughput screening techniques to allow rapid identification of useful compounds and monitor the effectiveness of treatment with a drug candidate (see, for example, Zlokarnik, et al., Science 279, 84-8 (1998)). Drug candidates may be chemical compounds, nucleic acids, proteins, antibodies, or derivatives therefrom, whether naturally occurring or synthetically derived. Drug candidates thus identified may be utilized, among other uses, as pharmaceutical compositions for administration to patients or for use in further screening assays.

Administration of a composition of the present invention to a host may be accomplished using any of a variety of techniques known to those of skill in the art. The composition(s) may be processed in accordance with conventional methods of pharmacy to produce medicinal agents for administration to patients, including humans and other mammals (i.e., a "pharmaceutical composition"). The pharmaceutical composition is preferably made in the form of a dosage unit containing a given amount of DNA, viral vector particles, polypeptide or peptide, for example. A suitable daily dose for a human or other mammal may vary widely depending on the condition of the patient and other factors, but, once again, can be determined using routine methods.

The pharmaceutical composition may be administered orally, parentally, by inhalation spray, rectally, intranodally, or topically in dosage unit formulations containing conventional pharmaceutically acceptable carriers, adjuvants, and vehicles. The term "pharmaceutically acceptable carrier" or "physiologically acceptable carrier" as used herein refers to one or more formulation materials suitable for accomplishing or enhancing the delivery of a nucleic acid, polypeptide, or peptide as a pharmaceutical composition. A "pharmaceutical composition" is a composition comprising a therapeutically effective amount of a nucleic acid or polypeptide. The terms "effective amount" and "therapeutically effective amount" each refer to the amount of a nucleic acid or polypeptide used to induce or enhance an effective immune response. It is preferred that compositions of the present invention provide for the induction or enhancement of an anti-tumor immune response in a host which protects the host from the development of a tumor and/or allows the host to eliminate an existing tumor from the body.

For oral administration, the pharmaceutical composition may be of any of several forms including, for example, a capsule, a tablet, a suspension, or liquid, among others. Liquids may be administered by injection as a composition with suitable carriers including saline, dextrose, or water. The term parenteral as used herein includes subcutaneous, intravenous, intramuscular, intrasternal, infusion, or intraperitoneal administration. Suppositories for rectal administration of the drug can be prepared by mixing the drug with a suitable non-irritating excipient such as cocoa butter and polyethylene glycols that are solid at ordinary temperatures but liquid at the rectal temperature.

The dosage regimen for immunizing a host or otherwise treating a disorder or a disease with a composition of this invention is based on a variety of factors, including the type of disease, the age, weight, sex, medical condition of the patient, the severity of the condition, the route of administration, and the particular compound employed. For example, a poxviral vector may be administered as a composition comprising $1 \times 10^6$ infectious particles per dose. Thus, the dosage regimen may vary widely, but can be determined routinely using standard methods.

A prime-boost regimen may also be utilized (see, for example, WO 01/30382 A1) in which the targeted immunogen is initially administered in a priming step in one form followed by a boosting step in which the targeted immunogen is administered in another form. The form of the targeted immunogen in the priming and boosting steps are different. For instance, if the priming step utilized a nucleic acid, the boost may be administered as a peptide. Similarly, where a priming step utilized one type of recombinant virus (i.e., ALVAC), the boost step may utilize another type of virus (i.e., NYVAC). This prime-boost method of administration has been shown to induce strong immunological responses.

While the compositions of the invention can be administered as the sole active pharmaceutical agent, they can also be used in combination with one or more other compositions or agents (i.e., other immunogenic targets, co-stimulatory molecules, adjuvants). When administered as a combination, the individual components can be formulated as separate compositions administered at the same time or different times, or the components can be combined as a single composition.

Injectable preparations, such as sterile injectable aqueous or oleaginous suspensions, may be formulated according to known methods using suitable dispersing or wetting agents and suspending agents. The injectable preparation may also be a sterile injectable solution or suspension in a non-toxic parenterally acceptable diluent or solvent. Suitable vehicles and solvents that may be employed are water, Ringer's solution, and isotonic sodium chloride solution, among others. For instance, a viral vector such as a poxvirus may be prepared in 0.4% NaCl. In addition, sterile, fixed oils are conventionally employed as a solvent or suspending medium. For this purpose, any bland fixed oil may be employed, including synthetic mono- or diglycerides. In addition, fatty acids such as oleic acid find use in the preparation of injectables.

For topical administration, a suitable topical dose of a composition may be administered one to four, and preferably two or three times daily. The dose may also be administered with intervening days during which no does is applied. Suitable compositions may comprise from 0.001% to 10% w/w, for example, from 1% to 2% by weight of the formulation, although it may comprise as much as 10% w/w, but preferably not more than 5% w/w, and more preferably from 0.1% to 1% of the formulation. Formulations suitable for topical administration include liquid or semi-liquid preparations suitable for penetration through the skin (e.g., liniments, lotions, ointments, creams, or pastes) and drops suitable for administration to the eye, ear, or nose.

The pharmaceutical compositions may also be prepared in a solid form (including granules, powders or suppositories). The pharmaceutical compositions may be subjected to conventional pharmaceutical operations such as sterilization and/or may contain conventional adjuvants, such as preservatives, stabilizers, wetting agents, emulsifiers, buffers etc. Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings. Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting sweetening, flavoring, and perfuming agents.

Pharmaceutical compositions comprising a nucleic acid or polypeptide of the present invention may take any of several forms and may be administered by any of several routes. In preferred embodiments, the compositions are administered via a parenteral route (intradermal, intramuscular or subcutaneous) to induce an immune response in the host. Alternatively, the composition may be administered directly into a lymph node (intranodal) or tumor mass (i.e., intratumoral administration). For example, the dose could be administered subcutaneously at days 0, 7, and 14. Suitable methods for immunization using compositions comprising TAs are known in the art, as shown for p53 (Hollstein et al., 1991), p21-ras (Almoguera et al., 19S8), HER-2 (Fendly et al., 1990), the melanoma-associated antigens (MAGE-1; MAGE-2) (van der Bruggen et al., 1991), p97 (Hu et al., 1988), melanoma-associated antigen E (WO 99/30737) and carcinoembryonic antigen (CEA) (Kantor et al., 1993; Fishbein et al., 1992; Kaufman et al., 1991), among others.

Preferred embodiments of administratable compositions include, for example, nucleic acids or polypeptides in liquid preparations such as suspensions, syrups, or elixirs. Preferred injectable preparations include, for example, nucleic acids or polypeptides suitable for parental, subcutaneous, intradermal, intramuscular or intravenous administration such as sterile suspensions or emulsions. For example, a recombinant poxvirus may be in admixture with a suitable carrier, diluent, or excipient such as sterile water, physiological saline, glucose or the like. The composition may also be provided in lyophilized form for reconstituting, for instance, in isotonic aqueous, saline buffer. In addition, the compositions can be co-administered or sequentially administered with other antineoplastic, anti-tumor or anti-cancer agents and/or with agents which reduce or alleviate ill effects of antineoplastic, anti-tumor or anti-cancer agents.

A kit comprising a composition of the present invention is also provided. The kit can include a separate container containing a suitable carrier, diluent or excipient. The kit can also include an additional anti-cancer, anti-tumor or antineoplastic agent and/or an agent that reduces or alleviates ill effects of antineoplastic, anti-tumor or anti-cancer agents for co- or sequential-administration. Additionally, the kit can include instructions for mixing or combining ingredients and/or administration.

A better understanding of the present invention and of its many advantages will be had from the following examples, given by way of illustration.

EXAMPLES

Example 1

BFA5 Breast Cancer Antigen

A. Identification of BFA5

Microarray profiling analysis indicated that BFA5 was expressed at low to high levels in 41 out of 54 breast tumor biopsy samples (76%) and at high levels in 31 out of 54 breast tumors (57%), as compared to a panel of 52 normal, non-tumor tissues. In situ hybridization (ISH) was performed using a series of BFA5 DNA probes and confirmed the microarray with at least 61% of the tumors showing fairly strong signals. Further bioinformatics assessment confirmed the results of these gene expression analysis results.

Sequence analysis of the BFA5 nucleotide sequence revealed a high degree of similarity to two unidentified human genes: KIAA1074 (GenBank Accession No. XM_159732); and, KIAA0565 (GenBank Accession No. AB011137) isolated from a number of fetal and adult brain cDNA clones (Kikuno, et al. The complete sequences of 100 new cDNA clones from brain which code for large proteins in vitro. *DNA Res.* 6: 197-205). These genes were found to contain putative Zn finger regions and a nuclear localization sequence. BFA5 was suggested by others to be a potential breast cancer antigen (Jager, et al. 2001. Identification of a tissue-specific putative transcription factor in breast tissue by serological screening of a breast cancer library. *Cancer Res.* 61: 2055-2061 and WO 01/47959). In each of these publications, the nucleotide sequence BFA5 was designated NYBR-1 ("New York Breast Cancer-1"; GenBank Accession Nos. AF269087 (nucleotide) and AAK27325 (amino acid).

As shown previously by Jager, et al. and described in WO 01/47959, supra, BFA5 is specifically expressed in mammary gland, being expressed in $^{12}/_{19}$ breast tumors analyzed. The structure of the BFA5/NYBR-1 gene has revealed that it encodes a 150-160 kD nuclear transcription factor with a bZIP site (DNA-binding domain followed by a leucine zipper motif). The gene also contains 5 tandem ankyrin repeats implying a role in protein-protein interactions. These ankyrin repeats may play a role in homo-dimerization of the protein. The BFA5 cDNA sequence is shown in FIG. 4 and SEQ ID NO.: 5. The BFA5 amino acid sequence is shown in FIG. 5 and SEQ ID NO.: 6.

B. Immunoreactivity of BFA5

1. Activation of Human T Cells and IFN-γ Secretion in ELISPOT.

A library of 100 peptides from the BFA5/NYBR-1 coding sequence that are predicted to be medium to high binders to HLA-A*0201 were designed using Rammensee and Parker algorithms. The library was sub-divided into 10 pools of ten peptides (Table III), and each pool was used to activate 10 different T cell cultures after pulsing peptides on to mature autologous dendritic cells. Two experiments were performed with the library of BFA5/NYBR-1 peptides demonstrating immunoreactivity in HLA-A*0201 human T cells, as described below.

TABLE III

BFA5 Peptide Pools

| Peptide Group | CLP number | Sequence | SEQ ID |
|---|---|---|---|
| BFA5 Group 1 | 2983 | LMDMQTFKA | 7 |
| | 2984 | KVSIPTKAL | 8 |
| | 2985 | SIPTKALEL | 9 |
| | 2986 | LELKNEQTL | 10 |
| | 2987 | TVSQKDVCL | 11 |
| | 2988 | SVPNKALEL | 12 |
| | 2989 | CETVSQKDV | 13 |
| | 2990 | KINGKLEES | 14 |
| | 2991 | SLVEKTPDE | 15 |
| | 2992 | SLCETVSQK | 16 |
| BFA5 Group 2 | 2993 | EIDKINGKL | 17 |
| | 2994 | MLLQQNVDV | 18 |
| | 2995 | NMWLQQQLV | 19 |
| | 2996 | FLVDRKCQL | 20 |
| | 2997 | YLLHENCML | 21 |
| | 2998 | SLFESSAKI | 22 |
| | 2999 | KITIDIHFL | 23 |
| | 3000 | QLQSKNMWL | 24 |
| | 3001 | SLDQKLFQL | 25 |
| | 3002 | FLLIKNANA | 26 |
| BFA5 Group 3 | 3003 | KILDTVHSC | 27 |
| | 3004 | SLSKILDTV | 28 |
| | 3005 | ILIDSGADI | 29 |
| | 3006 | KVMEINREV | 30 |
| | 3007 | KLLSHGAVI | 31 |
| | 3009 | AVYSEILSV | 32 |
| | 3010 | KMNVDVSST | 33 |
| | 3011 | ILSVVAKLL | 34 |
| | 3012 | VLIAENTML | 35 |
| BFA5 Group 4 | 3013 | KLSKNHQNT | 36 |
| | 3014 | SLTPLLLSI | 37 |
| | 3015 | SQYSGQLKV | 38 |
| | 3016 | KELEVKQQL | 39 |
| | 3017 | QIMEYIRKL | 40 |
| | 3018 | AMLKLEIAT | 41 |
| | 3019 | VLHQPLSEA | 42 |
| | 3020 | GLLKATCGM | 43 |
| | 3021 | GLLKANCGM | 44 |
| | 3022 | QQLEQALRI | 45 |
| BFA5 Group 5 | 3023 | CMLKKEIAM | 46 |
| | 3024 | EQMKKKFCV | 47 |
| | 3025 | IQDIELKSV | 48 |
| | 3026 | SVPNKAFEL | 49 |
| | 3027 | SIYQKVMEI | 50 |
| | 3028 | NLNYAGDAL | 51 |
| | 3029 | AVQDHDQIV | 52 |
| BFA5 Group 6 | 3033 | FESSAKIQV | 53 |
| | 3034 | GVTAEHYAV | 54 |
| | 3035 | RVTSNKTKV | 55 |
| | 3036 | TVSQKDVCV | 56 |
| | 3037 | KSQEPAFHI | 57 |
| | 3038 | KVLIAENTM | 58 |
| | 3039 | MLKLEIATL | 59 |
| | 3040 | EILSVVAKL | 60 |
| | 3041 | MLKKEIAML | 61 |
| | 3042 | LLKEKNEEI | 62 |
| BFA5 Group 7 | 3043 | ALRIQDIEL | 63 |
| | 3044 | KIREELGRI | 64 |
| | 3045 | TLKLKEESL | 65 |
| | 3046 | ILNEKIREE | 66 |
| | 3047 | VLKKKLSEA | 67 |
| | 3048 | GTSDKIQCL | 68 |
| | 3049 | GADINLVDV | 69 |
| | 3050 | ELCSVRLTL | 70 |
| | 3051 | SVESNLNQV | 71 |
| | 3052 | SLKINLNYA | 72 |
| BFA5 Group 8 | 3053 | KTPDEAASL | 73 |
| | 3054 | ATCGMKVSI | 74 |
| | 3055 | LSHGAVIEV | 75 |
| | 3056 | EIAMLKLEI | 76 |
| | 3057 | AELQMTLKL | 77 |
| | 3058 | VFAADICGV | 78 |
| | 3060 | PAIEMQNSV | 79 |
| | 3061 | EIFNYNNHL | 80 |
| | 3062 | ILKEKNAEL | 81 |
| BFA5 Group 9 | 3063 | QLVHAHKKA | 82 |
| | 3065 | NIQDAQKRT | 83 |
| | 3066 | NLVDVYGNM | 84 |
| | 3067 | KCTALMLAV | 85 |
| | 3068 | KIQCLEKAT | 86 |
| | 3069 | KIAWEKKET | 87 |
| | 3070 | IAWEKKEDT | 88 |
| | 3071 | VGMLLQQNV | 89 |
| | 3072 | VKTGCVARV | 90 |
| BFA5 Group 10 | 3074 | ALHYAVYSE | 91 |
| | 3075 | QMKKKFCVL | 92 |
| | 3076 | ALQCHQEAC | 93 |
| | 3077 | SEQIVEFLL | 94 |
| | 3078 | AVIEVHNKA | 95 |
| | 3079 | AVTCGFHHI | 96 |
| | 3080 | ACLQRKMNV | 97 |
| | 3081 | SLVEGTSDK | 98 |

ELISPOT analysis was performed on human T-cell cultures activated through four rounds of stimulation with each pool of BFA5 peptides. Reactivity against a CMV pp 65 peptide and a Flu matrix peptide were used as positive controls for T-cell activation in the experiments. Each experiment was performed with PBMC and dendritic cells from a single HLA-A*0201+ donor designated as "AP10". The results show that, although BFA4 is markedly reactive with high ELISPOT counts per 100,000 cells in the assay, BFA5 is even more reactive with 9/10 pools demonstrating ELISPOT reactivity. Similar results were obtained for both BFA4 and BFA5/NYBR-1 with a different HLA-A*0201. The bars reach a maximum at 600 spots because beyond that the ELISPOT reader does not give accurate counts. Cultures having a reading of 600 spots have more than this number of spots.

A large number of the BFA5 peptide pools of are reactive as shown by the high levels of IFN-γ production. Each reactive peptide pool was then separated into individual peptides and analyzed for immunogencity using ELISPOT analysis to isolate single reactive BFA5 peptides. BFA5 is highly immunogenic with several reactive single peptides than that of BFA4. Similar results were obtained in two independent PBMC culture experiments.

In addition to ELISPOT analysis, human T cells activated by BFA5 peptides were assayed to determine their ability to function as CTL. The cells were activated using peptide-pulsed dendritic cells followed by CD40 ligand-activated B cells (5 rounds of stimulation). The experiment shown was performed with isolated PBMC from HLA-A*0201+ donor AP31. Isolated T cells were tested in $^{51}$Cr-release assays using peptide-loaded T2 cells. The % specific lysis at a 10:1, 5:1, and 1:1 T-cell to target ratio is shown for T2 cells pulsed with either pools of BFA5/NYBR-1 peptides or with individual peptides. The graph shows CTL activity induced against targets loaded with a c non-specific HLA-A*0201-binding HIV peptide (control) followed by the CTL activity against the peptide pool (Pool 1 etc.) and then the activity induced by individual peptides from the respective pool to the right. A high level of cytotoxicity was observed for some peptides at a 1:1 E:T ratio. CTL activity (percent specific lysis) induced by the control HIV peptide was generally <10%. Similar results were obtained with another PBMC donor expressing HLA-A*0201 (AP10). A large number of BFA5 peptides trigger T cell-mediated cytotoxicity of BFA5 peptide-loaded target cells. Table IV lists those peptides having immunogenic properties. Five peptides (LMDMQTFKA (SEQ ID NO.:7), ILIDSGADI (SEQ ID NO.:29), ILSVVAKLL (SEQ ID NO.:34), SQYSGQLKV (SEQ ID NO.:38), and ELCSVRLTL (SEQ ID NO.:70)) were found to induce both IFN-γ secretion and CTL activity in T cells from both donors.

TABLE IV

Immunoreactive peptides from BFA5

| | BFA5 peptides eliciting high IFN-γ release (>200 spots/100,000 cells) | | BFA5 peptides inducing CTL lysis of pulsed cells | |
|---|---|---|---|---|
| SEQ ID NO. | Donor AP10 | Donor AP31 | Donor AP10 | Donor AP31 |
| 7 | LMDMQTFKA | LMDMQTFKA | LMDMQTFKA | LMDMQTFKA |
| 8 | KVSIPTKAL | | | KVSIPTKAL |
| 9 | SIPTKALEL | | | SIPTKALEL |
| 11 | TVSQKDVCL | | | |
| 12 | SVPNKALEL | | | |
| 21 | YLLHENCML | YLLHENCML | YLLHENCML | |
| 24 | QLQSKNMWL | QLQSKNMWL | | QLQSKNMWL |
| 28 | SLSKILDTV | SLSKILDTV | | SLSKILDTV |
| 29 | ILIDSGADI | ILIDSGADI | ILIDSGADI | ILIDSGADI |
| 30 | KVMEINREV | | | |
| 32 | AVYSEILSV | | | |
| 34 | ILSVVAKLL | ILSVVAKLL | ILSVVAKLL | ILSVVAKLL |
| 37 | SLTPLLLSI | SLTPLLLSI | | SLTPLLLSI |
| 38 | SQYSGQLKV | SQYSGQLKV | SQYSGQLKV | SQYSGQLKV |
| 40 | QIMEYIRKL | QIMEYIRKL | | QIMEYIRKL |
| 49 | SVPNKAFEL | | | |
| 51 | NLNYAGDAL | NLNYAGDAL | | |
| 54 | | GVTAEHYAV | | |
| 57 | | KSQEPAFHI | | |
| 59 | MLKLEIATL | MLKLEIATL | | MLKLEIATL |
| 61 | | MLKKEIAML | | |
| 63 | ALRIQDIEL | | | |
| 67 | | VLKKKLSEA | | |
| 70 | ELCSVRLTL | ELCSVRLTL | ELCSVRLTL | ELCSVRLTL |
| 72 | SLKINLNYA | SLKINLNYA | | SLKINLNVA |
| 74 | ATCGMKVSI | | ATCGMKVSI | |
| 77 | AELQMTLKL | | AELQMTLKL | AELQMTLKL |
| 78 | | VFAADICGV | | |
| 81 | ILKEKNAEL | ILKEKNAEL | | |
| 84 | NLVDVYGNM | | NLVDVYGNM | |
| 85 | KCTALMLAV | | | |

C. Immunological Reagents

Polyclonal antisera were generated against the following series of 22- to 23-mer peptides of BFA5:

```
BFA5(1-23)                            (CLP-2977;
KLH-MTKRKKTINLNIQDAQKRTALHW           SEQ ID NO: 99)

BFA5(312-334)                         (CLP-2978;
KLH-TSEKFTWPAKGRPRKIAWEKKED           SEQ ID NO: 100)

BFA5(612-634)                         (CLP-2979;
KLH-DEILPSESKQKDYEENSWDTESL           SEQ ID NO: 101)

BFA5(972-994)                         (CLP-2980;
KLH-RLTLNQEEEKRRNADILNEKIRE           SEQ ID NO: 102)

BFAS(1117-1139)                       (CLP-2981;
KLH-AENTMLTSKLKEKQDKEILEAEI           SEQ ID NO: 103)

BFA5(1319-1341)                       (CLP-2982;
KLH-NYNNHLKNRIYQYEKEKAETENS           SEQ ID NO: 104)
```

Prebleed samples from rabbits were processed and stored at −20° C. Rabbits were immunized as follows: 1) the peptides were administered as an emulsion with Freund's Complete Adjuvant (FCA); and, 2) two weeks later, the peptides were coupled with Keyhole-Limpet Hemocyanin (KLH)-coupled and administered as an emulsion with Freund's Incomplete Adjuvant FIA. The following results were observed:

TABLE V

| Peptide/protein | IgG titer × $10^5$ (After first Immunization Rb1/Rb2) | IgG titer × $10^5$ (After second Immunization Rb1/Rb2) |
|---|---|---|
| CLP 2977 | 25/6 | 256/64 |
| CLP 2978 | 25/25 | 64/256 |
| CLP 2979 | 12/25 | 256/512 |
| CLP 2980 | 25/12 | 1024/128 |
| CLP 2981 | 8/4 | 256/64 |
| CLP 2982 | 2/2 | 64/32 |

Prebleed sample results exhibited IgG titers <100 for all samples.

To assess the quality of the polyclonal antisera, western blots were performed using sera against BFA5. Sera were separately screened against cell extracts obtained from the BT474, MDMB453, MCF-7, Calu-6, and CosA2 cells. The approximate expected MWr of BFA5 protein is 153 kDa. A 220 kDA band was observed in the BT474 extract with CLP2980 antibody but not in the MDMB453 cell extracts however a ~130 kD band was present in the MDMB453 extract. Both bands were found to be consistent with the polyclonal antisera tested in this analysis. Neither of these bands is present in the negative control. Thus, it can be concluded that the polyclonal antisera are specific for BFA5.

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. An isolated peptide selected from the group consisting of SEQ ID NO.:7, SEQ ID NO.:8, SEQ ID NO.:9, SEQ ID NO.:11, and SEQ ID NO.:12, the peptide being immunogenic as determined by ELISPOT analysis of human T-cell cultures or human T cell cytotoxicity assay.

2. A composition comprising an isolated peptide of claim 1 and a pharmaceutically acceptable carrier.

3. The isolated peptide LMDMQTFKA (SEQ ID NO.:7).

4. A composition comprising the isolated peptide of claim 3 in a pharmaceutically acceptable carrier.

5. A composition for inducing an immune response in a host comprising the isolated peptide of claim 3 and at least one isolated peptide selected from the group consisting of SEQ ID NO.:8, SEQ ID NO.:9, SEQ ID NO.:11, SEQ ID NO.:12, SEQ ID NO.:21, SEQ ID NO.:24, SEQ ID NO.:29, SEQ ID NO.:30, SEQ ID NO.:32, SEQ ID NO.:34, SEQ ID NO.:37, SEQ ID NO.:38, SEQ ID NO.:40, SEQ ID NO.:49, SEQ ID NO.:51, SEQ ID NO.:54, SEQ ID NO.:57, SEQ ID NO.:59, SEQ ID NO.:61, SEQ ID NO.:63, SEQ ID NO.:67, SEQ ID NO.:70, SEQ ID NO.:72, SEQ ID NO.:74, SEQ ID NO.:77, SEQ ID NO.:78, SEQ ID NO.:81, SEQ ID NO.:84, SEQ ID NO.:85, SEQ ID NO.:99, SEQ ID NO.:100, SEQ ID NO.:101, SEQ ID NO.:102, SEQ ID NO.:103, and SEQ ID NO.:104, and a pharmaceutically acceptable carrier.

6. A method for inducing an immune response against the tumor antigen BFA5 (SEQ ID NO.: 6) in a host comprising administering to the host the isolated peptide of claim 3.

7. A method for inducing an immune response against the tumor antigen BFA5 (SEQ ID NO.: 6) in a host comprising administering to the host the composition of claim 4.

8. A method for inducing an immune response in a host against the tumor antigen BFA5 (SEQ ID NO.: 6) comprising administering to the host the composition of claim 5.

* * * * *

SEQUENCE LISTING

<160> NUMBER OF SEQ ID NOS: 105

<210> SEQ ID NO 1
<211> LENGTH: 3846
<212> TYPE: DNA
<213> ORGANISM: Homo sapiens

<400> SEQUENCE: 1

```
atggtccgga aaagaaccc ccctctgaga acgttgcaa gtgaaggcga gggccagatc      60
ctggagccta taggtacaga aagcaaggta tctggaaaga caaagaatt ctctgcagat    120
cagatgtcag aaaatacgga tcagagtgat gctgcagaac taaatcataa ggaggaacat   180
agcttgcatg ttcaagatcc atcttctagc agtaagaagg acttgaaaag cgcagttctg   240
agtgagaagg ctggcttcaa ttatgaaagc cccagtaagg aggaaacttt ccctccttt   300
ccgcatgatg aggtgacaga cagaaatatg ttggctttct catttccagc tgctggggga   360
gtctgtgagc ccttgaagtc tccgcaaaga gcagaggcag atgaccctca agatatggcc   420
tgcaccccct caggggactc actggagaca aaggaagatc agaagatgtc accaaaggct   480
acagaggaaa cagggcaagc acagagtggt caagccaatt gtcaaggttt gagcccagtt   540
tcagtggcct caaaaaaccc acaagtgcct tcagatgggg gtgtaagact gaataaatcc   600
aaaactgact tactggtgaa tgacaaccca gacccggcac ctctgtctcc agagcttcag   660
gactttaaat gcaatatctg tggatatggt tactacggca acgacccac agatctgatt   720
aagcacttcc gaaagtatca cttaggactg cataaccgca ccaggcaaga tgctgagctg   780
gacagcaaaa tcttggccct tcataacatg gtgcagttca gccattccaa agacttccag   840
aaggtcaacc gttctgtgtt ttctggtgtg ctgcaggaca tcaattcttc aaggcctgtt   900
ttactaaatg ggacctatga tgtgcaggtg acttcaggtg gaacattcat tggcattgga   960
cggaaaacac cagattgcca agggaacacc aagtatttcc gctgtaaatt ctgcaatttc   1020
acttatatgg gcaactcatc caccgaatta gaacaacatt ttcttcagac tcacccaaac   1080
aaaataaaag cttctctccc ctcctctgag gttgcaaaac cttcagagaa aaactctaac   1140
aagtccatcc ctgcacttca atccagtgat tctggagact gggaaaatg caggacaag    1200
ataacagtca aagcaggaga tgacactcct gttgggtact cagtgcccat aaagcccctc   1260
gattcctcta gacaaaatgg tacagaggcc accagttact actggtgtaa attttgtagt   1320
ttcagctgtg agtcatctag ctcacttaaa ctgctagaac attatggcaa gcagcacgga   1380
gcagtgcagt caggcggcct taatccagag ttaaatgata agctttccag gggctctgtc   1440
attaatcaga atgatctagc caaaagttca gaaggagaga caatgaccaa gacagacaag   1500
agctcgagtg gggctaaaaa gaaggacttc tccagcaagg gagccgagga taatatggta   1560
acgagctata attgtcagtt ctgtgacttc cgatattcca aaagccatgg ccctgatgta   1620
attgtagtgg ggccacttct ccgtcattat caacagctcc ataacattca aagtgtacc   1680
attaaacact gtccattctg tcccagagga ctttgcagcc agaaaagca ccttggagaa    1740
attacttatc cgtttgcttg tagaaaaagt aattgttccc actgtgcact cttgcttctg   1800
cacttgtctc ctgggcggc tggaagctcg cgagtcaaac atcagtgcca tcagtgttca   1860
ttcaccaccc ctgacgtaga tgtactcctc tttcactatg aaagtgtgca tgagtcccaa   1920
gcatcggatg tcaaacaaga agcaaatcac ctgcaaggat cggatgggca gcagtctgtc   1980
aaggaaagca agaacactc atgtaccaaa tgtgatttta ttacccaagt ggaagaagag   2040
```

| | |
|---|---|
| atttcccgac actacaggag agcacacagc tgctacaaat gccgtcagtg cagtttttaca | 2100 |
| gctgccgata ctcagtcact actggagcac ttcaacactg ttcactgcca ggaacaggac | 2160 |
| atcactacag ccaacggcga agaggacggt catgccatat ccaccatcaa agaggagccc | 2220 |
| aaaattgact tcagggtcta caatctgcta actccagact ctaaaatggg agagccagtt | 2280 |
| tctgagagtg tggtgaagag agaagctg gaagagaagg acgggctcaa agagaaagtt | 2340 |
| tggaccgaga gttccagtga tgaccttcgc aatgtgactt ggagaggggc agacatcctg | 2400 |
| cgggggagtc cgtcatacac ccaagcaagc ctggggctgc tgacgcctgt gtctggcacc | 2460 |
| caagagcaga caaagactct aagggatagt cccaatgtgg aggccgccca tctggcgcga | 2520 |
| cctatttatg gcttggctgt ggaaaccaag ggattcctgc aggggggcgcc agctggcgga | 2580 |
| gagaagtctg ggccctccc ccagcagtat cctgcatcgg gagaaaacaa gtccaaggat | 2640 |
| gaatcccagt ccctgttacg gaggcgtaga ggctccggtg ttttttgtgc caattgcctg | 2700 |
| accacaaaga cctctctctg gcgaaagaat gcaaatggcg gatatgtatg caacgcgtgt | 2760 |
| ggcctctacc agaagcttca ctcgactccc aggcctttaa acatcattaa acaaaacaac | 2820 |
| ggtgagcaga ttattaggag gagaacaaga aagcgcctta acccagaggc acttcaggct | 2880 |
| gagcagctca acaaacagca gaggggcagc aatgaggagc aagtcaatgg aagcccgtta | 2940 |
| gagaggaggt cagaagatca tctaactgaa agtcaccaga gagaaattcc actccccagc | 3000 |
| ctaagtaaat acgaagccca gggttcattg actaaaagcc attctgctca gcagccagtc | 3060 |
| ctggtcagcc aaactctgga tattcacaaa aggatgcaac ctttgcacat tcagataaaa | 3120 |
| agtcctcagg aaagtactgg agatccagga aatagttcat ccgtatctga agggaaagga | 3180 |
| agttctgaga gaggcagtcc tatagaaaag tacatgagac ctgcgaaaca cccaaattat | 3240 |
| tcaccaccag gcagccctat tgaaaagtac cagtacccac ttttggact tccctttgta | 3300 |
| cataatgact tccagagtga agctgattgg ctgcggttct ggagtaaata taagctctcc | 3360 |
| gttcctggga atccgcacta cttgagtcac gtgcctggcc taccaaatcc ttgccaaaac | 3420 |
| tatgtgcctt atcccacctt caatctgcct cctcattttt cagctgttgg atcagacaat | 3480 |
| gacattcctc tagatttggc gatcaagcat tccagacctg gccaactgc aaacggtgcc | 3540 |
| tccaaggaga aaacgaaggc accaccaaat gtaaaaaatg aaggtcccctt gaatgtagta | 3600 |
| aaaacagaga aagttgatag aagtactcaa gatgaacttt caacaaaatg tgtgcactgt | 3660 |
| ggcattgtct ttctggatga agtgatgtat gcttttgcata tgagttgcca tggtgacagt | 3720 |
| ggaccttttcc agtgcagcat atgccagcat cttttgcacgg acaaatatga cttcacaaca | 3780 |
| catatccaga ggggcctgca taggaacaat gcacaagtgg aaaaaaatgg aaaacctaaa | 3840 |
| gagtaa | 3846 |

<210> SEQ ID NO 2
<211> LENGTH: 1281
<212> TYPE: PRT
<213> ORGANISM: Homo sapiens

<400> SEQUENCE: 2

Met Val Arg Lys Lys Asn Pro Pro Leu Arg Asn Val Ala Ser Glu Gly
1               5                   10                  15

Glu Gly Gln Ile Leu Glu Pro Ile Gly Thr Glu Ser Lys Val Ser Gly
            20                  25                  30

Lys Asn Lys Glu Phe Ser Ala Asp Gln Met Ser Glu Asn Thr Asp Gln
        35                  40                  45

Ser Asp Ala Ala Glu Leu Asn His Lys Glu Glu His Ser Leu His Val

-continued

```
                50                  55                  60
Gln Asp Pro Ser Ser Ser Lys Lys Asp Leu Lys Ser Ala Val Leu
 65                  70                  75                  80

Ser Glu Lys Ala Gly Phe Asn Tyr Glu Ser Pro Ser Lys Gly Gly Asn
                     85                  90                  95

Phe Pro Ser Phe Pro His Asp Glu Val Thr Asp Arg Asn Met Leu Ala
                100                 105                 110

Phe Ser Phe Pro Ala Ala Gly Gly Val Cys Glu Pro Leu Lys Ser Pro
                115                 120                 125

Gln Arg Ala Glu Ala Asp Asp Pro Gln Asp Met Ala Cys Thr Pro Ser
130                 135                 140

Gly Asp Ser Leu Glu Thr Lys Glu Asp Gln Lys Met Ser Pro Lys Ala
145                 150                 155                 160

Thr Glu Glu Thr Gly Gln Ala Gln Ser Gly Gln Ala Asn Cys Gln Gly
                165                 170                 175

Leu Ser Pro Val Ser Val Ala Ser Lys Asn Pro Gln Val Pro Ser Asp
                180                 185                 190

Gly Gly Val Arg Leu Asn Lys Ser Lys Thr Asp Leu Leu Val Asn Asp
                195                 200                 205

Asn Pro Asp Pro Ala Pro Leu Ser Pro Glu Leu Gln Asp Phe Lys Cys
210                 215                 220

Asn Ile Cys Gly Tyr Gly Tyr Tyr Gly Asn Asp Pro Thr Asp Leu Ile
225                 230                 235                 240

Lys His Phe Arg Lys Tyr His Leu Gly Leu His Asn Arg Thr Arg Gln
                245                 250                 255

Asp Ala Glu Leu Asp Ser Lys Ile Leu Ala Leu His Asn Met Val Gln
                260                 265                 270

Phe Ser His Ser Lys Asp Phe Gln Lys Val Asn Arg Ser Val Phe Ser
                275                 280                 285

Gly Val Leu Gln Asp Ile Asn Ser Ser Arg Pro Val Leu Leu Asn Gly
                290                 295                 300

Thr Tyr Asp Val Gln Val Thr Ser Gly Gly Thr Phe Ile Gly Ile Gly
305                 310                 315                 320

Arg Lys Thr Pro Asp Cys Gln Gly Asn Thr Lys Tyr Phe Arg Cys Lys
                325                 330                 335

Phe Cys Asn Phe Thr Tyr Met Gly Asn Ser Ser Thr Glu Leu Glu Gln
                340                 345                 350

His Phe Leu Gln Thr His Pro Asn Lys Ile Lys Ala Ser Leu Pro Ser
                355                 360                 365

Ser Glu Val Ala Lys Pro Ser Glu Lys Asn Ser Asn Lys Ser Ile Pro
370                 375                 380

Ala Leu Gln Ser Ser Asp Ser Gly Asp Leu Gly Lys Trp Gln Asp Lys
385                 390                 395                 400

Ile Thr Val Lys Ala Gly Asp Asp Thr Pro Val Gly Tyr Ser Val Pro
                405                 410                 415

Ile Lys Pro Leu Asp Ser Ser Arg Gln Asn Gly Thr Glu Ala Thr Ser
                420                 425                 430

Tyr Tyr Trp Cys Lys Phe Cys Ser Phe Ser Cys Glu Ser Ser Ser Ser
                435                 440                 445

Leu Lys Leu Leu Glu His Tyr Gly Lys Gln His Gly Ala Val Gln Ser
                450                 455                 460

Gly Gly Leu Asn Pro Glu Leu Asn Asp Lys Leu Ser Arg Gly Ser Val
465                 470                 475                 480
```

-continued

```
Ile Asn Gln Asn Asp Leu Ala Lys Ser Ser Glu Gly Glu Thr Met Thr
                485                 490                 495

Lys Thr Asp Lys Ser Ser Ser Gly Ala Lys Lys Lys Asp Phe Ser Ser
            500                 505                 510

Lys Gly Ala Glu Asp Asn Met Val Thr Ser Tyr Asn Cys Gln Phe Cys
        515                 520                 525

Asp Phe Arg Tyr Ser Lys Ser His Gly Pro Asp Val Ile Val Val Gly
    530                 535                 540

Pro Leu Leu Arg His Tyr Gln Gln Leu His Asn Ile His Lys Cys Thr
545                 550                 555                 560

Ile Lys His Cys Pro Phe Cys Pro Arg Gly Leu Cys Ser Pro Glu Lys
                565                 570                 575

His Leu Gly Glu Ile Thr Tyr Pro Phe Ala Cys Arg Lys Ser Asn Cys
            580                 585                 590

Ser His Cys Ala Leu Leu Leu His Leu Ser Pro Gly Ala Ala Gly
        595                 600                 605

Ser Ser Arg Val Lys His Gln Cys His Gln Cys Ser Phe Thr Thr Pro
    610                 615                 620

Asp Val Asp Val Leu Leu Phe His Tyr Glu Ser Val His Glu Ser Gln
625                 630                 635                 640

Ala Ser Asp Val Lys Gln Glu Ala Asn His Leu Gln Gly Ser Asp Gly
                645                 650                 655

Gln Gln Ser Val Lys Glu Ser Lys Glu His Ser Cys Thr Lys Cys Asp
            660                 665                 670

Phe Ile Thr Gln Val Glu Glu Ile Ser Arg His Tyr Arg Arg Ala
    675                 680                 685

His Ser Cys Tyr Lys Cys Arg Gln Cys Ser Phe Thr Ala Ala Asp Thr
    690                 695                 700

Gln Ser Leu Leu Glu His Phe Asn Thr Val His Cys Gln Glu Gln Asp
705                 710                 715                 720

Ile Thr Thr Ala Asn Gly Glu Glu Asp Gly His Ala Ile Ser Thr Ile
                725                 730                 735

Lys Glu Glu Pro Lys Ile Asp Phe Arg Val Tyr Asn Leu Leu Thr Pro
            740                 745                 750

Asp Ser Lys Met Gly Glu Pro Val Ser Glu Ser Val Val Lys Arg Glu
        755                 760                 765

Lys Leu Glu Glu Lys Asp Gly Leu Lys Glu Lys Val Trp Thr Glu Ser
    770                 775                 780

Ser Ser Asp Asp Leu Arg Asn Val Thr Trp Arg Gly Ala Asp Ile Leu
785                 790                 795                 800

Arg Gly Ser Pro Ser Tyr Thr Gln Ala Ser Leu Gly Leu Leu Thr Pro
                805                 810                 815

Val Ser Gly Thr Gln Glu Gln Thr Lys Thr Leu Arg Asp Ser Pro Asn
            820                 825                 830

Val Glu Ala Ala His Leu Ala Arg Pro Ile Tyr Gly Leu Ala Val Glu
        835                 840                 845

Thr Lys Gly Phe Leu Gln Gly Ala Pro Ala Gly Gly Glu Lys Ser Gly
    850                 855                 860

Ala Leu Pro Gln Gln Tyr Pro Ala Ser Gly Glu Asn Lys Ser Lys Asp
865                 870                 875                 880

Glu Ser Gln Ser Leu Leu Arg Arg Arg Gly Ser Gly Val Phe Cys
                885                 890                 895

Ala Asn Cys Leu Thr Thr Lys Thr Ser Leu Trp Arg Lys Asn Ala Asn
            900                 905                 910
```

```
Gly Gly Tyr Val Cys Asn Ala Cys Gly Leu Tyr Gln Lys Leu His Ser
            915                 920                 925

Thr Pro Arg Pro Leu Asn Ile Ile Lys Gln Asn Asn Gly Glu Gln Ile
        930                 935                 940

Ile Arg Arg Arg Thr Arg Lys Arg Leu Asn Pro Glu Ala Leu Gln Ala
945                 950                 955                 960

Glu Gln Leu Asn Lys Gln Gln Arg Gly Ser Asn Glu Glu Gln Val Asn
            965                 970                 975

Gly Ser Pro Leu Glu Arg Arg Ser Glu Asp His Leu Thr Glu Ser His
        980                 985                 990

Gln Arg Glu Ile Pro Leu Pro Ser  Leu Ser Lys Tyr Glu  Ala Gln Gly
        995                 1000                1005

Ser Leu  Thr Lys Ser His Ser  Ala Gln Gln Pro Val  Leu Val Ser
        1010                1015                1020

Gln Thr  Leu Asp Ile His Lys  Arg Met Gln Pro Leu  His Ile Gln
        1025                1030                1035

Ile Lys  Ser Pro Gln Glu Ser  Thr Gly Asp Pro Gly  Asn Ser Ser
        1040                1045                1050

Ser Val  Ser Glu Gly Lys Gly  Ser Ser Glu Arg Gly  Ser Pro Ile
        1055                1060                1065

Glu Lys  Tyr Met Arg Pro Ala  Lys His Pro Asn Tyr  Ser Pro Pro
        1070                1075                1080

Gly Ser  Pro Ile Glu Lys Tyr  Gln Tyr Pro Leu Phe  Gly Leu Pro
        1085                1090                1095

Phe Val  His Asn Asp Phe Gln  Ser Glu Ala Asp Trp  Leu Arg Phe
        1100                1105                1110

Trp Ser  Lys Tyr Lys Leu Ser  Val Pro Gly Asn Pro  His Tyr Leu
        1115                1120                1125

Ser His  Val Pro Gly Leu Pro  Asn Pro Cys Gln Asn  Tyr Val Pro
        1130                1135                1140

Tyr Pro  Thr Phe Asn Leu Pro  Pro His Phe Ser Ala  Val Gly Ser
        1145                1150                1155

Asp Asn  Asp Ile Pro Leu Asp  Leu Ala Ile Lys His  Ser Arg Pro
        1160                1165                1170

Gly Pro  Thr Ala Asn Gly Ala  Ser Lys Glu Lys Thr  Lys Ala Pro
        1175                1180                1185

Pro Asn  Val Lys Asn Glu Gly  Pro Leu Asn Val Val  Lys Thr Glu
        1190                1195                1200

Lys Val  Asp Arg Ser Thr Gln  Asp Glu Leu Ser Thr  Lys Cys Val
        1205                1210                1215

His Cys  Gly Ile Val Phe Leu  Asp Glu Val Met Tyr  Ala Leu His
        1220                1225                1230

Met Ser  Cys His Gly Asp Ser  Gly Pro Phe Gln Cys  Ser Ile Cys
        1235                1240                1245

Gln His  Leu Cys Thr Asp Lys  Tyr Asp Phe Thr Thr  His Ile Gln
        1250                1255                1260

Arg Gly  Leu His Arg Asn Asn  Ala Gln Val Glu Lys  Asn Gly Lys
        1265                1270                1275

Pro Lys  Glu
        1280

<210> SEQ ID NO 3
<211> LENGTH: 1203
<212> TYPE: DNA
```

<213> ORGANISM: Homo sapiens

<400> SEQUENCE: 3

```
atggccgagc tgcgcctgaa gggcagcagc aacaccacgg agtgtgttcc cgtgcccacc      60
tccgagcacg tggccgagat cgtgggcagg caaggctgca agattaaggc cttgagggcc     120
aagaccaaca cctacatcaa gaccggtg agggcgagg aaccagtgtt catggtgaca         180
gggcgacggg aggacgtggc cacagcccgg cggaaaatca tctcagcagc ggagcacttc     240
tccatgatcc gtgcctcccg caacaagtca ggcgccgcct ttggtgtggc cctgctctg     300
cccggccagt gaccatccg tgtgcgggtg ccctaccgcg tggtggggct ggtggtgggc      360
cccaaagggg caaccatcaa gcgcatccag cagcaaacca acacatacat tatcacacca     420
agccgtgacc gcgaccccgt gttcgagatc acgggtgccc caggcaacgt ggagcgtgcg     480
cgcgaggaga tcgagacgca catcgcggtg cgcactggca agatcctcga gtacaacaat     540
gaaaacgact tcctggcggg gagccccgac gcagcaatcg atagccgcta ctccgacgcc     600
tggcgggtgc accagcccgg ctgcaagccc ctctccacct tccggcagaa cagcctgggc     660
tgcatcggcg agtgcggagt ggactctggc tttgaggccc cacgcctggg tgagcagggc     720
ggggactttg gctacggcgg gtacctcttt ccgggctatg gcgtgggcaa gcaggatgtg     780
tactacggcg tggccgagac tagccccccg ctgtgggcgg gccaggagaa cgccacgccc     840
acctccgtgc tcttctcctc tgcctcctcc tcctcctcct cttccgccaa ggcccgcgct     900
gggcccccgg gcgcacaccg ctcccctgcc acttccgcgg acccgagct ggccggactc      960
ccgaggcgcc ccccgggaga gccgctccag ggcttctcta acttggtgg gggcggcctg    1020
cggagccccg gcggcgggcg ggattgcatg gtctgctttg agagcgaagt gactgccgcc    1080
cttgtgccct gcggacacaa cctgttctgc atggagtgtg cagtacgcat ctgcgagagg    1140
acggacccag agtgtcccgt ctgccacatc acagccgcgc aagccatccg aatattctcc    1200
taa                                                                  1203
```

<210> SEQ ID NO 4
<211> LENGTH: 400
<212> TYPE: PRT
<213> ORGANISM: Homo sapiens

<400> SEQUENCE: 4

```
Met Ala Glu Leu Arg Leu Lys Gly Ser Ser Asn Thr Thr Glu Cys Val
1               5                   10                  15

Pro Val Pro Thr Ser Glu His Val Ala Glu Ile Val Gly Arg Gln Gly
            20                  25                  30

Cys Lys Ile Lys Ala Leu Arg Ala Lys Thr Asn Thr Tyr Ile Lys Thr
        35                  40                  45

Pro Val Arg Gly Glu Glu Pro Val Phe Met Val Thr Gly Arg Arg Glu
    50                  55                  60

Asp Val Ala Thr Ala Arg Arg Glu Ile Ile Ser Ala Ala Glu His Phe
65                  70                  75                  80

Ser Met Ile Arg Ala Ser Arg Asn Lys Ser Gly Ala Ala Phe Gly Val
                85                  90                  95

Ala Pro Ala Leu Pro Gly Gln Val Thr Ile Arg Val Arg Val Pro Tyr
            100                 105                 110

Arg Val Val Gly Leu Val Val Gly Pro Lys Gly Ala Thr Ile Lys Arg
        115                 120                 125

Ile Gln Gln Gln Thr Asn Thr Tyr Ile Ile Thr Pro Ser Arg Asp Arg
    130                 135                 140
```

```
Asp Pro Val Phe Glu Ile Thr Gly Ala Pro Gly Asn Val Glu Arg Ala
145                 150                 155                 160

Arg Glu Glu Ile Glu Thr His Ile Ala Val Arg Thr Gly Lys Ile Leu
            165                 170                 175

Glu Tyr Asn Asn Glu Asn Asp Phe Leu Ala Gly Ser Pro Asp Ala Ala
            180                 185                 190

Ile Asp Ser Arg Tyr Ser Asp Ala Trp Arg Val His Gln Pro Gly Cys
        195                 200                 205

Lys Pro Leu Ser Thr Phe Arg Gln Asn Ser Leu Gly Cys Ile Gly Glu
210                 215                 220

Cys Gly Val Asp Ser Gly Phe Glu Ala Pro Arg Leu Gly Glu Gln Gly
225                 230                 235                 240

Gly Asp Phe Gly Tyr Gly Gly Tyr Leu Phe Pro Gly Tyr Gly Val Gly
                245                 250                 255

Lys Gln Asp Val Tyr Tyr Gly Val Ala Glu Thr Ser Pro Pro Leu Trp
            260                 265                 270

Ala Gly Gln Glu Asn Ala Thr Pro Thr Ser Val Leu Phe Ser Ser Ala
        275                 280                 285

Ser Ser Ser Ser Ser Ser Ala Lys Ala Arg Ala Gly Pro Pro Gly
290                 295                 300

Ala His Arg Ser Pro Ala Thr Ser Ala Gly Pro Glu Leu Ala Gly Leu
305                 310                 315                 320

Pro Arg Arg Pro Pro Gly Glu Pro Leu Gln Gly Phe Ser Lys Leu Gly
                325                 330                 335

Gly Gly Gly Leu Arg Ser Pro Gly Gly Arg Asp Cys Met Val Cys
            340                 345                 350

Phe Glu Ser Glu Val Thr Ala Ala Leu Val Pro Cys Gly His Asn Leu
        355                 360                 365

Phe Cys Met Glu Cys Ala Val Arg Ile Cys Glu Arg Thr Asp Pro Glu
370                 375                 380

Cys Pro Val Cys His Ile Thr Ala Ala Gln Ala Ile Arg Ile Phe Ser
385                 390                 395                 400

<210> SEQ ID NO 5
<211> LENGTH: 4026
<212> TYPE: DNA
<213> ORGANISM: Homo sapiens

<400> SEQUENCE: 5
atgacaaaga ggaagaagac catcaacctt aatatacaag acgcccagaa gaggactgct      60
ctacactggg cctgtgtcaa tggccatgag gaagtagtaa catttctggt agacagaaag     120
tgccagcttg acgtccttga tggcgaacac aggacacctc tgatgaaggc tctacaatgc     180
catcaggagg cttgtgcaaa tattctgata gattctggtg ccgatataaa tctcgtagat     240
gtgtatggca acatggctct ccattatgct gtttatagtg agattttgtc agtggtggca     300
aaactgctgt cccatggtgc agtcatcgaa gtgcacaaca aggctagcct cacaccactt     360
ttactatcca taacgaaaag aagtgagcaa attgtgaat ttttgctgat aaaaaatgca     420
aatgcgaatg cagttaataa gtataaatgc acagccctca tgcttgctgt atgtcatgga     480
tcatcagaga tagttggcat gcttcttcag caaaatgttg acgtctttgc tgcagatata     540
tgtggagtaa ctgcagaaca ttatgctgtt acttgtggat tcatcacat tcatgaacaa     600 attatggaat atacgaaaa attatctaaa aatcatcaaa ataccaatcc agaaggaaca     660
tctgcaggaa cacctgatga ggctgcaccc ttggcggaaa gaacacctga cacagctgaa     720
```

```
agcttggtgg aaaaaacacc tgatgaggct gcacccttgg tggaaagaac acctgacacg      780
gctgaaagct tggtggaaaa aacacctgat gaggctgcat ccttggtgga gggaacatct      840
gacaaaattc aatgtttgga gaaagcgaca tctggaaagt tcgaacagtc agcagaagaa      900
acacctaggg aaattacgag tcctgcaaaa gaaacatctg agaaatttac gtggccagca      960
aaaggaagac ctaggaagat cgcatggag aaaaagaag acacacctag ggaaattatg       1020
agtcccgcaa agaaacatc tgagaaattt acgtgggcag caaaaggaag acctaggaag      1080
atcgcatggg agaaaaaaga acacctgta aagactggat gcgtggcaag agtaacatct      1140
aataaaacta agttttgga aaaggaaga tctaagatga ttgcatgtcc tacaaaagaa       1200
tcatctacaa agcaagtgc caatgatcag aggttcccat cagaatccaa acaagaggaa      1260
gatgaagaat attcttgtga ttctcggagt ctctttgaga gttctgcaaa gattcaagtg     1320
tgtatacctg agtctatata tcaaaaagta atggagataa atagagaagt agaagagcct     1380
cctaagaagc catctgcctt caagcctgcc attgaaatgc aaaactctgt tccaaataaa     1440
gcctttgaat tgaagaatga acaaacattg agagcagatc cgatgttccc accagaatcc     1500
aaacaaaagg actatgaaga aaattcttgg gattctgaga gtctctgtga gactgtttca     1560
cagaaggatg tgtgtttacc caaggctaca catcaaaaag aaatagataa aataaatgga     1620
aaattagaag agtctcctaa taagatggt cttctgaagg ctacctgcgg aatgaaagtt      1680
tctattccaa ctaaagcctt agaattgaag gacatgcaaa ctttcaaagc ggagcctccg     1740
gggaagccat ctgccttcga gcctgccact gaaatgcaaa agtctgtccc aaataaagcc     1800
ttggaattga aaatgaaca acatggaga gcagatgaga tactcccatc agaatccaaa       1860
caaaaggact atgaagaaaa ttcttgggat actgagagtc tctgtgagac tgtttcacag     1920
aaggatgtgt gtttacccaa ggctgcgcat caaaagaaa tagataaaat aaatggaaaa      1980
ttagaagggt ctcctgttaa agatggtctt ctgaaggcta actgcggaat gaaagtttct     2040
attccaacta agccttaga attgatggac atgcaaactt caaagcaga gcctcccgag       2100 aagccatctg ccttcgagcc tgccattgaa atgcaaaagt ctgttccaaa taaagccttg     2160
gaattgaaga tgaacaaac attgagagca gatgagatac tcccatcaga atccaaacaa      2220
aaggactatg aagaaagttc ttgggattct gagagtctct gtgagactgt ttcacagaag     2280
gatgtgtgtt tacccaaggc tacacatcaa aagaaatag ataaataaa tggaaaatta      2340 gaagagtctc ctgataatga tggttttctg aaggctccct gcagaatgaa agtttctatt     2400
ccaactaaag ccttagaatt gatggacatg caaactttca aagcagagcc tcccgagaag     2460
ccatctgcct tcgagcctgc cattgaaatg caaaagtctg ttccaaataa agccttggaa     2520
ttgaagaatg aacaaacatt gagagcagat cagatgttcc cttcagaatc aaaacaaaag     2580
aaggttgaag aaaattcttg ggattctgag agtctccgtg agactgtttc acagaaggat     2640
gtgtgtgtac ccaaggctac acatcaaaaa gaaatggata aataagtgg aaaattagaa      2700 gattcaacta gcctatcaaa aatcttggat acagttcatt cttgtgaaag agcagggaa      2760 cttcaaaaag atcactgtga acaacgtaca ggaaaaatgg aacaaatgaa aaagaagttt     2820
tgtgtactga aaagaaact gtcagaagca aagaaataa atcacagtt agagaaccaa       2880 aaagttaaat gggaacaaga gctctgcagt gtgagattga ctttaaacca agaagaagag     2940
aagagaagaa atgccgatat attaaatgaa aaaattaggg aagaattagg aagaatcgaa     3000
gagcagcata ggaaagagtt agaagtgaaa caacaacttg aacaggctct cagaatacaa     3060
gatatagaat tgaagagtgt agaaagtaat ttgaatcagg tttctcacac tcatgaaaat     3120
```

```
gaaaattatc tcttacatga aaattgcatg ttgaaaaagg aaattgccat gctaaaactg    3180
gaaatagcca cactgaaaca ccaataccag gaaaggaaa ataaatactt tgaggacatt     3240
aagattttaa aagaaaagaa tgctgaactt cagatgaccc taaaactgaa agaggaatca    3300
ttaactaaaa gggcatctca atatagtggg cagcttaaag ttctgatagc tgagaacaca    3360
atgctcactt ctaaattgaa ggaaaaacaa gacaaagaaa tactagaggc agaaattgaa    3420
tcacaccatc ctagactggc ttctgctgta caagaccatg atcaaattgt gacatcaaga    3480
aaaagtcaag aacctgcttt ccacattgca ggagatgctt gtttgcaaag aaaaatgaat    3540
gttgatgtga gtagtacgat atataacaat gaggtgctcc atcaaccact ttctgaagct    3600
caaaggaaat ccaaaagcct aaaaattaat ctcaattatg caggagatgc tctaagagaa    3660
aatacattgg tttcagaaca tgcacaaaga gaccaacgtg aaacacagtg tcaaatgaag    3720
gaagctgaac acatgtatca aaacgaacaa gataatgtga acaaacacac tgaacagcag    3780
gagtctctag atcagaaatt atttcaacta caaagcaaaa atatgtggct tcaacagcaa    3840
ttagttcatg cacataagaa agctgacaac aaaagcaaga taacaattga tattcattt     3900 cttgagagga aaatgcaaca tcatctccta aagagaaaa atgaggagat atttaattac     3960
aataaccatt taaaaaaccg tatatatcaa tatgaaaaag agaaagcaga aacagaaaac    4020
tcatga                                                              4026
```

<210> SEQ ID NO 6
<211> LENGTH: 1341
<212> TYPE: PRT
<213> ORGANISM: Homo sapiens

<400> SEQUENCE: 6

```
Met Thr Lys Arg Lys Lys Thr Ile Asn Leu Asn Ile Gln Asp Ala Gln
1               5                   10                  15

Lys Arg Thr Ala Leu His Trp Ala Cys Val Asn Gly His Glu Glu Val
            20                  25                  30

Val Thr Phe Leu Val Asp Arg Lys Cys Gln Leu Asp Val Leu Asp Gly
        35                  40                  45

Glu His Arg Thr Pro Leu Met Lys Ala Leu Gln Cys His Gln Glu Ala
    50                  55                  60

Cys Ala Asn Ile Leu Ile Asp Ser Gly Ala Asp Ile Asn Leu Val Asp
65                  70                  75                  80

Val Tyr Gly Asn Met Ala Leu His Tyr Ala Val Tyr Ser Glu Ile Leu
                85                  90                  95

Ser Val Val Ala Lys Leu Leu Ser His Gly Ala Val Ile Glu Val His
            100                 105                 110

Asn Lys Ala Ser Leu Thr Pro Leu Leu Leu Ser Ile Thr Lys Arg Ser
        115                 120                 125

Glu Gln Ile Val Glu Phe Leu Leu Ile Lys Asn Ala Asn Ala Asn Ala
    130                 135                 140

Val Asn Lys Tyr Lys Cys Thr Ala Leu Met Leu Ala Val Cys His Gly
145                 150                 155                 160

Ser Ser Glu Ile Val Gly Met Leu Leu Gln Gln Asn Val Asp Val Phe
                165                 170                 175

Ala Ala Asp Ile Cys Gly Val Thr Ala Glu His Tyr Ala Val Thr Cys
            180                 185                 190

Gly Phe His His Ile His Glu Gln Ile Met Glu Tyr Ile Arg Lys Leu
        195                 200                 205
```

-continued

| | | | | | | | | | | | | | |
|---|---|---|---|---|---|---|---|---|---|---|---|---|---|
|Ser|Lys|Asn|His|Gln|Asn|Thr|Asn|Pro|Glu|Gly|Thr|Ser|Ala|Gly|Thr|
| |210| | | |215| | | |220| | | | | |

Ser Lys Asn His Gln Asn Thr Asn Pro Glu Gly Thr Ser Ala Gly Thr
    210                 215                 220

Pro Asp Glu Ala Ala Pro Leu Ala Glu Arg Thr Pro Asp Thr Ala Glu
225                 230                 235                 240

Ser Leu Val Glu Lys Thr Pro Asp Glu Ala Ala Pro Leu Val Glu Arg
                245                 250                 255

Thr Pro Asp Thr Ala Glu Ser Leu Val Glu Lys Thr Pro Asp Glu Ala
                260                 265                 270

Ala Ser Leu Val Glu Gly Thr Ser Asp Lys Ile Gln Cys Leu Glu Lys
                275                 280                 285

Ala Thr Ser Gly Lys Phe Glu Gln Ser Ala Glu Thr Pro Arg Glu
                290                 295                 300

Ile Thr Ser Pro Ala Lys Glu Thr Ser Glu Lys Phe Thr Trp Pro Ala
305                 310                 315                 320

Lys Gly Arg Pro Arg Lys Ile Ala Trp Glu Lys Lys Glu Asp Thr Pro
                325                 330                 335

Arg Glu Ile Met Ser Pro Ala Lys Glu Thr Ser Glu Lys Phe Thr Trp
                340                 345                 350

Ala Ala Lys Gly Arg Pro Arg Lys Ile Ala Trp Glu Lys Lys Glu Thr
                355                 360                 365

Pro Val Lys Thr Gly Cys Val Ala Arg Val Thr Ser Asn Lys Thr Lys
                370                 375                 380

Val Leu Glu Lys Gly Arg Ser Lys Met Ile Ala Cys Pro Thr Lys Glu
385                 390                 395                 400

Ser Ser Thr Lys Ala Ser Ala Asn Asp Gln Arg Phe Pro Ser Glu Ser
                405                 410                 415

Lys Gln Glu Glu Asp Glu Glu Tyr Ser Cys Asp Ser Arg Ser Leu Phe
                420                 425                 430

Glu Ser Ser Ala Lys Ile Gln Val Cys Ile Pro Glu Ser Ile Tyr Gln
                435                 440                 445

Lys Val Met Glu Ile Asn Arg Glu Val Glu Glu Pro Pro Lys Lys Pro
                450                 455                 460

Ser Ala Phe Lys Pro Ala Ile Glu Met Gln Asn Ser Val Pro Asn Lys
465                 470                 475                 480

Ala Phe Glu Leu Lys Asn Glu Gln Thr Leu Arg Ala Asp Pro Met Phe
                485                 490                 495

Pro Pro Glu Ser Lys Gln Lys Asp Tyr Glu Glu Asn Ser Trp Asp Ser
                500                 505                 510

Glu Ser Leu Cys Glu Thr Val Ser Gln Lys Asp Val Cys Leu Pro Lys
                515                 520                 525

Ala Thr His Gln Lys Glu Ile Asp Lys Ile Asn Gly Lys Leu Glu Glu
                530                 535                 540

Ser Pro Asn Lys Asp Gly Leu Leu Lys Ala Thr Cys Gly Met Lys Val
545                 550                 555                 560

Ser Ile Pro Thr Lys Ala Leu Glu Leu Lys Asp Met Gln Thr Phe Lys
                565                 570                 575

Ala Glu Pro Pro Gly Lys Pro Ser Ala Phe Glu Pro Thr Glu Met
                580                 585                 590

Gln Lys Ser Val Pro Asn Lys Ala Leu Glu Leu Lys Asn Glu Gln Thr
                595                 600                 605

Trp Arg Ala Asp Glu Ile Leu Pro Ser Glu Ser Lys Gln Lys Asp Tyr
                610                 615                 620

Glu Glu Asn Ser Trp Asp Thr Glu Ser Leu Cys Glu Thr Val Ser Gln
625                 630                 635                 640

-continued

Lys Asp Val Cys Leu Pro Lys Ala Ala His Gln Lys Glu Ile Asp Lys
            645                 650                 655

Ile Asn Gly Lys Leu Glu Gly Ser Pro Val Lys Asp Gly Leu Leu Lys
            660                 665                 670

Ala Asn Cys Gly Met Lys Val Ser Ile Pro Thr Lys Ala Leu Glu Leu
            675                 680                 685

Met Asp Met Gln Thr Phe Lys Ala Glu Pro Glu Lys Pro Ser Ala
            690                 695                 700

Phe Glu Pro Ala Ile Glu Met Gln Lys Ser Val Pro Asn Lys Ala Leu
705                 710                 715                 720

Glu Leu Lys Asn Glu Gln Thr Leu Arg Ala Asp Glu Ile Leu Pro Ser
            725                 730                 735

Glu Ser Lys Gln Lys Asp Tyr Glu Glu Ser Ser Trp Asp Ser Glu Ser
            740                 745                 750

Leu Cys Glu Thr Val Ser Gln Lys Asp Val Cys Leu Pro Lys Ala Thr
            755                 760                 765

His Gln Lys Glu Ile Asp Lys Ile Asn Gly Lys Leu Glu Glu Ser Pro
            770                 775                 780

Asp Asn Asp Gly Phe Leu Lys Ala Pro Cys Arg Met Lys Val Ser Ile
785                 790                 795                 800

Pro Thr Lys Ala Leu Glu Leu Met Asp Met Gln Thr Phe Lys Ala Glu
            805                 810                 815

Pro Pro Glu Lys Pro Ser Ala Phe Glu Pro Ala Ile Glu Met Gln Lys
            820                 825                 830

Ser Val Pro Asn Lys Ala Leu Glu Leu Lys Asn Glu Gln Thr Leu Arg
            835                 840                 845

Ala Asp Gln Met Phe Pro Ser Glu Ser Lys Gln Lys Lys Val Glu Glu
            850                 855                 860

Asn Ser Trp Asp Ser Glu Ser Leu Arg Glu Thr Val Ser Gln Lys Asp
865                 870                 875                 880

Val Cys Val Pro Lys Ala Thr His Gln Lys Glu Met Asp Lys Ile Ser
            885                 890                 895

Gly Lys Leu Glu Asp Ser Thr Ser Leu Ser Lys Ile Leu Asp Thr Val
            900                 905                 910

His Ser Cys Glu Arg Ala Arg Glu Leu Gln Lys Asp His Cys Glu Gln
            915                 920                 925

Arg Thr Gly Lys Met Glu Gln Met Lys Lys Phe Cys Val Leu Lys
            930                 935                 940

Lys Lys Leu Ser Glu Ala Lys Glu Ile Lys Ser Gln Leu Glu Asn Gln
945                 950                 955                 960

Lys Val Lys Trp Glu Gln Glu Leu Cys Ser Val Arg Leu Thr Leu Asn
            965                 970                 975

Gln Glu Glu Glu Lys Arg Arg Asn Ala Asp Ile Leu Asn Glu Lys Ile
            980                 985                 990

Arg Glu Glu Leu Gly Arg Ile Glu Glu Gln His Arg Lys Glu Leu Glu
            995                 1000                1005

Val Lys Gln Gln Leu Glu Gln Ala Leu Arg Ile Gln Asp Ile Glu
            1010                1015                1020

Leu Lys Ser Val Glu Ser Asn Leu Asn Gln Val Ser His Thr His
            1025                1030                1035

Glu Asn Glu Asn Tyr Leu Leu His Glu Asn Cys Met Leu Lys Lys
            1040                1045                1050

Glu Ile Ala Met Leu Lys Leu Glu Ile Ala Thr Leu Lys His Gln

-continued

```
                1055                1060                1065

Tyr Gln Glu Lys Glu Asn Lys Tyr Phe Glu Asp Ile Lys Ile Leu
        1070                1075                1080

Lys Glu Lys Asn Ala Glu Leu Gln Met Thr Leu Lys Leu Lys Glu
        1085                1090                1095

Glu Ser Leu Thr Lys Arg Ala Ser Gln Tyr Ser Gly Gln Leu Lys
        1100                1105                1110

Val Leu Ile Ala Glu Asn Thr Met Leu Thr Ser Lys Leu Lys Glu
        1115                1120                1125

Lys Gln Asp Lys Glu Ile Leu Glu Ala Glu Ile Glu Ser His His
        1130                1135                1140

Pro Arg Leu Ala Ser Ala Val Gln Asp His Asp Gln Ile Val Thr
        1145                1150                1155

Ser Arg Lys Ser Gln Glu Pro Ala Phe His Ile Ala Gly Asp Ala
        1160                1165                1170

Cys Leu Gln Arg Lys Met Asn Val Asp Val Ser Ser Thr Ile Tyr
        1175                1180                1185

Asn Asn Glu Val Leu His Gln Pro Leu Ser Glu Ala Gln Arg Lys
        1190                1195                1200

Ser Lys Ser Leu Lys Ile Asn Leu Asn Tyr Ala Gly Asp Ala Leu
        1205                1210                1215

Arg Glu Asn Thr Leu Val Ser Glu His Ala Gln Arg Asp Gln Arg
        1220                1225                1230

Glu Thr Gln Cys Gln Met Lys Glu Ala Glu His Met Tyr Gln Asn
        1235                1240                1245

Glu Gln Asp Asn Val Asn Lys His Thr Glu Gln Gln Glu Ser Leu
        1250                1255                1260

Asp Gln Lys Leu Phe Gln Leu Gln Ser Lys Asn Met Trp Leu Gln
        1265                1270                1275

Gln Gln Leu Val His Ala His Lys Lys Ala Asp Asn Lys Ser Lys
        1280                1285                1290

Ile Thr Ile Asp Ile His Phe Leu Glu Arg Lys Met Gln His His
        1295                1300                1305

Leu Leu Lys Glu Lys Asn Glu Glu Ile Phe Asn Tyr Asn Asn His
        1310                1315                1320

Leu Lys Asn Arg Ile Tyr Gln Tyr Glu Lys Glu Lys Ala Glu Thr
        1325                1330                1335

Glu Asn Ser
        1340

<210> SEQ ID NO 7
<211> LENGTH: 9
<212> TYPE: PRT
<213> ORGANISM: Homo sapiens

<400> SEQUENCE: 7

Leu Met Asp Met Gln Thr Phe Lys Ala
1               5

<210> SEQ ID NO 8
<211> LENGTH: 9
<212> TYPE: PRT
<213> ORGANISM: Homo sapiens

<400> SEQUENCE: 8

Lys Val Ser Ile Pro Thr Lys Ala Leu
1               5
```

```
<210> SEQ ID NO 9
<211> LENGTH: 9
<212> TYPE: PRT
<213> ORGANISM: Homo sapiens

<400> SEQUENCE: 9

Ser Ile Pro Thr Lys Ala Leu Glu Leu
1               5

<210> SEQ ID NO 10
<211> LENGTH: 9
<212> TYPE: PRT
<213> ORGANISM: Homo sapiens

<400> SEQUENCE: 10

Leu Glu Leu Lys Asn Glu Gln Thr Leu
1               5

<210> SEQ ID NO 11
<211> LENGTH: 9
<212> TYPE: PRT
<213> ORGANISM: Homo sapiens

<400> SEQUENCE: 11

Thr Val Ser Gln Lys Asp Val Cys Leu
1               5

<210> SEQ ID NO 12
<211> LENGTH: 9
<212> TYPE: PRT
<213> ORGANISM: Homo sapiens

<400> SEQUENCE: 12

Ser Val Pro Asn Lys Ala Leu Glu Leu
1               5

<210> SEQ ID NO 13
<211> LENGTH: 9
<212> TYPE: PRT
<213> ORGANISM: Homo sapiens

<400> SEQUENCE: 13

Cys Glu Thr Val Ser Gln Lys Asp Val
1               5

<210> SEQ ID NO 14
<211> LENGTH: 9
<212> TYPE: PRT
<213> ORGANISM: Homo sapiens

<400> SEQUENCE: 14

Lys Ile Asn Gly Lys Leu Glu Glu Ser
1               5

<210> SEQ ID NO 15
<211> LENGTH: 9
<212> TYPE: PRT
<213> ORGANISM: Homo sapiens

<400> SEQUENCE: 15

Ser Leu Val Glu Lys Thr Pro Asp Glu
1               5

<210> SEQ ID NO 16
```

```
<211> LENGTH: 9
<212> TYPE: PRT
<213> ORGANISM: Homo sapiens

<400> SEQUENCE: 16

Ser Leu Cys Glu Thr Val Ser Gln Lys
1               5

<210> SEQ ID NO 17
<211> LENGTH: 9
<212> TYPE: PRT
<213> ORGANISM: Homo sapiens

<400> SEQUENCE: 17

Glu Ile Asp Lys Ile Asn Gly Lys Leu
1               5

<210> SEQ ID NO 18
<211> LENGTH: 9
<212> TYPE: PRT
<213> ORGANISM: Homo sapiens

<400> SEQUENCE: 18

Met Leu Leu Gln Gln Asn Val Asp Val
1               5

<210> SEQ ID NO 19
<211> LENGTH: 9
<212> TYPE: PRT
<213> ORGANISM: Homo sapiens

<400> SEQUENCE: 19

Asn Met Trp Leu Gln Gln Gln Leu Val
1               5

<210> SEQ ID NO 20
<211> LENGTH: 9
<212> TYPE: PRT
<213> ORGANISM: Homo sapiens

<400> SEQUENCE: 20

Phe Leu Val Asp Arg Lys Cys Gln Leu
1               5

<210> SEQ ID NO 21
<211> LENGTH: 9
<212> TYPE: PRT
<213> ORGANISM: Homo sapiens

<400> SEQUENCE: 21

Tyr Leu Leu His Glu Asn Cys Met Leu
1               5

<210> SEQ ID NO 22
<211> LENGTH: 9
<212> TYPE: PRT
<213> ORGANISM: Homo sapiens

<400> SEQUENCE: 22

Ser Leu Phe Glu Ser Ser Ala Lys Ile
1               5

<210> SEQ ID NO 23
<211> LENGTH: 9
<212> TYPE: PRT
<213> ORGANISM: Homo sapiens
```

```
<400> SEQUENCE: 23

Lys Ile Thr Ile Asp Ile His Phe Leu
1               5

<210> SEQ ID NO 24
<211> LENGTH: 9
<212> TYPE: PRT
<213> ORGANISM: Homo sapiens

<400> SEQUENCE: 24

Gln Leu Gln Ser Lys Asn Met Trp Leu
1               5

<210> SEQ ID NO 25
<211> LENGTH: 9
<212> TYPE: PRT
<213> ORGANISM: Homo sapiens

<400> SEQUENCE: 25

Ser Leu Asp Gln Lys Leu Phe Gln Leu
1               5

<210> SEQ ID NO 26
<211> LENGTH: 9
<212> TYPE: PRT
<213> ORGANISM: Homo sapiens

<400> SEQUENCE: 26

Phe Leu Leu Ile Lys Asn Ala Asn Ala
1               5

<210> SEQ ID NO 27
<211> LENGTH: 9
<212> TYPE: PRT
<213> ORGANISM: Homo sapiens

<400> SEQUENCE: 27

Lys Ile Leu Asp Thr Val His Ser Cys
1               5

<210> SEQ ID NO 28
<211> LENGTH: 9
<212> TYPE: PRT
<213> ORGANISM: Homo sapiens

<400> SEQUENCE: 28

Ser Leu Ser Lys Ile Leu Asp Thr Val
1               5

<210> SEQ ID NO 29
<211> LENGTH: 9
<212> TYPE: PRT
<213> ORGANISM: Homo sapiens

<400> SEQUENCE: 29

Ile Leu Ile Asp Ser Gly Ala Asp Ile
1               5

<210> SEQ ID NO 30
<211> LENGTH: 9
<212> TYPE: PRT
<213> ORGANISM: Homo sapiens

<400> SEQUENCE: 30
```

```
Lys Val Met Glu Ile Asn Arg Glu Val
1               5

<210> SEQ ID NO 31
<211> LENGTH: 9
<212> TYPE: PRT
<213> ORGANISM: Homo sapiens

<400> SEQUENCE: 31

Lys Leu Leu Ser His Gly Ala Val Ile
1               5

<210> SEQ ID NO 32
<211> LENGTH: 9
<212> TYPE: PRT
<213> ORGANISM: Homo sapiens

<400> SEQUENCE: 32

Ala Val Tyr Ser Glu Ile Leu Ser Val
1               5

<210> SEQ ID NO 33
<211> LENGTH: 9
<212> TYPE: PRT
<213> ORGANISM: Homo sapiens

<400> SEQUENCE: 33

Lys Met Asn Val Asp Val Ser Ser Thr
1               5

<210> SEQ ID NO 34
<211> LENGTH: 9
<212> TYPE: PRT
<213> ORGANISM: Homo sapiens

<400> SEQUENCE: 34

Ile Leu Ser Val Val Ala Lys Leu Leu
1               5

<210> SEQ ID NO 35
<211> LENGTH: 9
<212> TYPE: PRT
<213> ORGANISM: Homo sapiens

<400> SEQUENCE: 35

Val Leu Ile Ala Glu Asn Thr Met Leu
1               5

<210> SEQ ID NO 36
<211> LENGTH: 9
<212> TYPE: PRT
<213> ORGANISM: Homo sapiens

<400> SEQUENCE: 36

Lys Leu Ser Lys Asn His Gln Asn Thr
1               5

<210> SEQ ID NO 37
<211> LENGTH: 9
<212> TYPE: PRT
<213> ORGANISM: Homo sapiens

<400> SEQUENCE: 37

Ser Leu Thr Pro Leu Leu Leu Ser Ile
1               5
```

```
<210> SEQ ID NO 38
<211> LENGTH: 9
<212> TYPE: PRT
<213> ORGANISM: Homo sapiens

<400> SEQUENCE: 38

Ser Gln Tyr Ser Gly Gln Leu Lys Val
1               5

<210> SEQ ID NO 39
<211> LENGTH: 9
<212> TYPE: PRT
<213> ORGANISM: Homo sapiens

<400> SEQUENCE: 39

Lys Glu Leu Glu Val Lys Gln Gln Leu
1               5

<210> SEQ ID NO 40
<211> LENGTH: 9
<212> TYPE: PRT
<213> ORGANISM: Homo sapiens

<400> SEQUENCE: 40

Gln Ile Met Glu Tyr Ile Arg Lys Leu
1               5

<210> SEQ ID NO 41
<211> LENGTH: 9
<212> TYPE: PRT
<213> ORGANISM: Homo sapiens

<400> SEQUENCE: 41

Ala Met Leu Lys Leu Glu Ile Ala Thr
1               5

<210> SEQ ID NO 42
<211> LENGTH: 9
<212> TYPE: PRT
<213> ORGANISM: Homo sapiens

<400> SEQUENCE: 42

Val Leu His Gln Pro Leu Ser Glu Ala
1               5

<210> SEQ ID NO 43
<211> LENGTH: 9
<212> TYPE: PRT
<213> ORGANISM: Homo sapiens

<400> SEQUENCE: 43

Gly Leu Leu Lys Ala Thr Cys Gly Met
1               5

<210> SEQ ID NO 44
<211> LENGTH: 9
<212> TYPE: PRT
<213> ORGANISM: Homo sapiens

<400> SEQUENCE: 44

Gly Leu Leu Lys Ala Asn Cys Gly Met
1               5

<210> SEQ ID NO 45
<211> LENGTH: 9
```

```
<212> TYPE: PRT
<213> ORGANISM: Homo sapiens

<400> SEQUENCE: 45

Gln Gln Leu Glu Gln Ala Leu Arg Ile
1               5

<210> SEQ ID NO 46
<211> LENGTH: 9
<212> TYPE: PRT
<213> ORGANISM: Homo sapiens

<400> SEQUENCE: 46

Cys Met Leu Lys Lys Glu Ile Ala Met
1               5

<210> SEQ ID NO 47
<211> LENGTH: 9
<212> TYPE: PRT
<213> ORGANISM: Homo sapiens

<400> SEQUENCE: 47

Glu Gln Met Lys Lys Lys Phe Cys Val
1               5

<210> SEQ ID NO 48
<211> LENGTH: 9
<212> TYPE: PRT
<213> ORGANISM: Homo sapiens

<400> SEQUENCE: 48

Ile Gln Lys Ile Glu Leu Lys Ser Val
1               5

<210> SEQ ID NO 49
<211> LENGTH: 9
<212> TYPE: PRT
<213> ORGANISM: Homo sapiens

<400> SEQUENCE: 49

Ser Val Pro Asn Lys Ala Phe Glu Leu
1               5

<210> SEQ ID NO 50
<211> LENGTH: 9
<212> TYPE: PRT
<213> ORGANISM: Homo sapiens

<400> SEQUENCE: 50

Ser Ile Tyr Gln Lys Val Met Glu Ile
1               5

<210> SEQ ID NO 51
<211> LENGTH: 9
<212> TYPE: PRT
<213> ORGANISM: Homo sapiens

<400> SEQUENCE: 51

Asn Leu Asn Tyr Ala Gly Asp Ala Leu
1               5

<210> SEQ ID NO 52
<211> LENGTH: 9
<212> TYPE: PRT
<213> ORGANISM: Homo sapiens
```

```
<400> SEQUENCE: 52

Ala Val Gln Asp His Asp Gln Ile Val
1               5

<210> SEQ ID NO 53
<211> LENGTH: 9
<212> TYPE: PRT
<213> ORGANISM: Homo sapiens

<400> SEQUENCE: 53

Phe Glu Ser Ser Ala Lys Ile Gln Val
1               5

<210> SEQ ID NO 54
<211> LENGTH: 9
<212> TYPE: PRT
<213> ORGANISM: Homo sapiens

<400> SEQUENCE: 54

Gly Val Thr Ala Glu His Tyr Ala Val
1               5

<210> SEQ ID NO 55
<211> LENGTH: 9
<212> TYPE: PRT
<213> ORGANISM: Homo sapiens

<400> SEQUENCE: 55

Arg Val Thr Ser Asn Lys Thr Lys Val
1               5

<210> SEQ ID NO 56
<211> LENGTH: 9
<212> TYPE: PRT
<213> ORGANISM: Homo sapiens

<400> SEQUENCE: 56

Thr Val Ser Gln Lys Asp Val Cys Val
1               5

<210> SEQ ID NO 57
<211> LENGTH: 9
<212> TYPE: PRT
<213> ORGANISM: Homo sapiens

<400> SEQUENCE: 57

Lys Ser Gln Glu Pro Ala Phe His Ile
1               5

<210> SEQ ID NO 58
<211> LENGTH: 9
<212> TYPE: PRT
<213> ORGANISM: Homo sapiens

<400> SEQUENCE: 58

Lys Val Leu Ile Ala Glu Asn Thr Met
1               5

<210> SEQ ID NO 59
<211> LENGTH: 9
<212> TYPE: PRT
<213> ORGANISM: Homo sapiens

<400> SEQUENCE: 59

Met Leu Lys Leu Glu Ile Ala Thr Leu
```

```
1               5
```

<210> SEQ ID NO 60
<211> LENGTH: 9
<212> TYPE: PRT
<213> ORGANISM: Homo sapiens

<400> SEQUENCE: 60

```
Glu Ile Leu Ser Val Val Ala Lys Leu
1               5
```

<210> SEQ ID NO 61
<211> LENGTH: 9
<212> TYPE: PRT
<213> ORGANISM: Homo sapiens

<400> SEQUENCE: 61

```
Met Leu Lys Lys Glu Ile Ala Met Leu
1               5
```

<210> SEQ ID NO 62
<211> LENGTH: 9
<212> TYPE: PRT
<213> ORGANISM: Homo sapiens

<400> SEQUENCE: 62

```
Leu Leu Lys Glu Lys Asn Glu Glu Ile
1               5
```

<210> SEQ ID NO 63
<211> LENGTH: 9
<212> TYPE: PRT
<213> ORGANISM: Homo sapiens

<400> SEQUENCE: 63

```
Ala Leu Arg Ile Gln Asp Ile Glu Leu
1               5
```

<210> SEQ ID NO 64
<211> LENGTH: 9
<212> TYPE: PRT
<213> ORGANISM: Homo sapiens

<400> SEQUENCE: 64

```
Lys Ile Arg Glu Glu Leu Gly Arg Ile
1               5
```

<210> SEQ ID NO 65
<211> LENGTH: 9
<212> TYPE: PRT
<213> ORGANISM: Homo sapiens

<400> SEQUENCE: 65

```
Thr Leu Lys Leu Lys Glu Glu Ser Leu
1               5
```

<210> SEQ ID NO 66
<211> LENGTH: 9
<212> TYPE: PRT
<213> ORGANISM: Homo sapiens

<400> SEQUENCE: 66

```
Ile Leu Asn Glu Lys Ile Arg Glu Glu
1               5
```

```
<210> SEQ ID NO 67
<211> LENGTH: 9
<212> TYPE: PRT
<213> ORGANISM: Homo sapiens

<400> SEQUENCE: 67

Val Leu Lys Lys Lys Leu Ser Glu Ala
1               5

<210> SEQ ID NO 68
<211> LENGTH: 9
<212> TYPE: PRT
<213> ORGANISM: Homo sapiens

<400> SEQUENCE: 68

Gly Thr Ser Asp Lys Ile Gln Cys Leu
1               5

<210> SEQ ID NO 69
<211> LENGTH: 9
<212> TYPE: PRT
<213> ORGANISM: Homo sapiens

<400> SEQUENCE: 69

Gly Ala Asp Ile Asn Leu Val Asp Val
1               5

<210> SEQ ID NO 70
<211> LENGTH: 9
<212> TYPE: PRT
<213> ORGANISM: Homo sapiens

<400> SEQUENCE: 70

Glu Leu Cys Ser Val Arg Leu Thr Leu
1               5

<210> SEQ ID NO 71
<211> LENGTH: 9
<212> TYPE: PRT
<213> ORGANISM: Homo sapiens

<400> SEQUENCE: 71

Ser Val Glu Ser Asn Leu Asn Gln Val
1               5

<210> SEQ ID NO 72
<211> LENGTH: 9
<212> TYPE: PRT
<213> ORGANISM: Homo sapiens

<400> SEQUENCE: 72

Ser Leu Lys Ile Asn Leu Asn Tyr Ala
1               5

<210> SEQ ID NO 73
<211> LENGTH: 9
<212> TYPE: PRT
<213> ORGANISM: Homo sapiens

<400> SEQUENCE: 73

Lys Thr Pro Asp Glu Ala Ala Ser Leu
1               5

<210> SEQ ID NO 74
<211> LENGTH: 9
<212> TYPE: PRT
```

```
<213> ORGANISM: Homo sapiens

<400> SEQUENCE: 74

Ala Thr Cys Gly Met Lys Val Ser Ile
1               5

<210> SEQ ID NO 75
<211> LENGTH: 9
<212> TYPE: PRT
<213> ORGANISM: Homo sapiens

<400> SEQUENCE: 75

Leu Ser His Gly Ala Val Ile Glu Val
1               5

<210> SEQ ID NO 76
<211> LENGTH: 9
<212> TYPE: PRT
<213> ORGANISM: Homo sapiens

<400> SEQUENCE: 76

Glu Ile Ala Met Leu Lys Leu Glu Ile
1               5

<210> SEQ ID NO 77
<211> LENGTH: 9
<212> TYPE: PRT
<213> ORGANISM: Homo sapiens

<400> SEQUENCE: 77

Ala Glu Leu Gln Met Thr Leu Lys Leu
1               5

<210> SEQ ID NO 78
<211> LENGTH: 9
<212> TYPE: PRT
<213> ORGANISM: Homo sapiens

<400> SEQUENCE: 78

Val Phe Ala Ala Asp Ile Cys Gly Val
1               5

<210> SEQ ID NO 79
<211> LENGTH: 9
<212> TYPE: PRT
<213> ORGANISM: Homo sapiens

<400> SEQUENCE: 79

Pro Ala Ile Glu Met Gln Asn Ser Val
1               5

<210> SEQ ID NO 80
<211> LENGTH: 9
<212> TYPE: PRT
<213> ORGANISM: Homo sapiens

<400> SEQUENCE: 80

Glu Ile Phe Asn Tyr Asn Asn His Leu
1               5

<210> SEQ ID NO 81
<211> LENGTH: 9
<212> TYPE: PRT
<213> ORGANISM: Homo sapiens

<400> SEQUENCE: 81
```

```
Ile Leu Lys Glu Lys Asn Ala Glu Leu
1               5
```

<210> SEQ ID NO 82
<211> LENGTH: 9
<212> TYPE: PRT
<213> ORGANISM: Homo sapiens

<400> SEQUENCE: 82

```
Gln Leu Val His Ala His Lys Lys Ala
1               5
```

<210> SEQ ID NO 83
<211> LENGTH: 9
<212> TYPE: PRT
<213> ORGANISM: Homo sapiens

<400> SEQUENCE: 83

```
Asn Ile Gln Asp Ala Gln Lys Arg Thr
1               5
```

<210> SEQ ID NO 84
<211> LENGTH: 9
<212> TYPE: PRT
<213> ORGANISM: Homo sapiens

<400> SEQUENCE: 84

```
Asn Leu Val Asp Val Tyr Gly Asn Met
1               5
```

<210> SEQ ID NO 85
<211> LENGTH: 9
<212> TYPE: PRT
<213> ORGANISM: Homo sapiens

<400> SEQUENCE: 85

```
Lys Cys Thr Ala Leu Met Leu Ala Val
1               5
```

<210> SEQ ID NO 86
<211> LENGTH: 9
<212> TYPE: PRT
<213> ORGANISM: Homo sapiens

<400> SEQUENCE: 86

```
Lys Ile Gln Cys Leu Glu Lys Ala Thr
1               5
```

<210> SEQ ID NO 87
<211> LENGTH: 9
<212> TYPE: PRT
<213> ORGANISM: Homo sapiens

<400> SEQUENCE: 87

```
Lys Ile Ala Trp Glu Lys Lys Glu Thr
1               5
```

<210> SEQ ID NO 88
<211> LENGTH: 9
<212> TYPE: PRT
<213> ORGANISM: Homo sapiens

<400> SEQUENCE: 88

```
Ile Ala Trp Glu Lys Lys Glu Asp Thr
1               5
```

```
<210> SEQ ID NO 89
<211> LENGTH: 9
<212> TYPE: PRT
<213> ORGANISM: Homo sapiens

<400> SEQUENCE: 373

Val Gly Met Leu Leu Gln Gln Asn Val
1               5

<210> SEQ ID NO 90
<211> LENGTH: 9
<212> TYPE: PRT
<213> ORGANISM: Homo sapiens

<400> SEQUENCE: 90

Val Lys Thr Gly Cys Val Ala Arg Val
1               5

<210> SEQ ID NO 91
<211> LENGTH: 9
<212> TYPE: PRT
<213> ORGANISM: Homo sapiens

<400> SEQUENCE: 91

Ala Leu His Tyr Ala Val Tyr Ser Glu
1               5

<210> SEQ ID NO 92
<211> LENGTH: 9
<212> TYPE: PRT
<213> ORGANISM: Homo sapiens

<400> SEQUENCE: 92

Gln Met Lys Lys Lys Phe Cys Val Leu
1               5

<210> SEQ ID NO 93
<211> LENGTH: 9
<212> TYPE: PRT
<213> ORGANISM: Homo sapiens

<400> SEQUENCE: 93

Ala Leu Gln Cys His Gln Glu Ala Cys
1               5

<210> SEQ ID NO 94
<211> LENGTH: 9
<212> TYPE: PRT
<213> ORGANISM: Homo sapiens

<400> SEQUENCE: 94

Ser Glu Gln Ile Val Glu Phe Leu Leu
1               5

<210> SEQ ID NO 95
<211> LENGTH: 9
<212> TYPE: PRT
<213> ORGANISM: Homo sapiens

<400> SEQUENCE: 95

Ala Val Ile Glu Val His Asn Lys Ala
1               5

<210> SEQ ID NO 96
```

```
<210> SEQ ID NO 96
<211> LENGTH: 9
<212> TYPE: PRT
<213> ORGANISM: Homo sapiens

<400> SEQUENCE: 96

Ala Val Thr Cys Gly Phe His His Ile
1               5

<210> SEQ ID NO 97
<211> LENGTH: 9
<212> TYPE: PRT
<213> ORGANISM: Homo sapiens

<400> SEQUENCE: 97

Ala Cys Leu Gln Arg Lys Met Asn Val
1               5

<210> SEQ ID NO 98
<211> LENGTH: 9
<212> TYPE: PRT
<213> ORGANISM: Homo sapiens

<400> SEQUENCE: 98

Ser Leu Val Glu Gly Thr Ser Asp Lys
1               5

<210> SEQ ID NO 99
<211> LENGTH: 23
<212> TYPE: PRT
<213> ORGANISM: Homo sapiens

<400> SEQUENCE: 99

Met Thr Lys Arg Lys Lys Thr Ile Asn Leu Asn Ile Gln Asp Ala Gln
1               5                   10                  15

Lys Arg Thr Ala Leu His Trp
            20

<210> SEQ ID NO 100
<211> LENGTH: 23
<212> TYPE: PRT
<213> ORGANISM: Homo sapiens

<400> SEQUENCE: 100

Thr Ser Glu Lys Phe Thr Trp Pro Ala Lys Gly Arg Pro Arg Lys Ile
1               5                   10                  15

Ala Trp Glu Lys Lys Glu Asp
            20

<210> SEQ ID NO 101
<211> LENGTH: 23
<212> TYPE: PRT
<213> ORGANISM: Homo sapiens

<400> SEQUENCE: 101

Asp Glu Ile Leu Pro Ser Glu Ser Lys Gln Lys Asp Tyr Glu Glu Asn
1               5                   10                  15

Ser Trp Asp Thr Glu Ser Leu
            20

<210> SEQ ID NO 102
<211> LENGTH: 23
<212> TYPE: PRT
<213> ORGANISM: Homo sapiens

<400> SEQUENCE: 102
```

```
Arg Leu Thr Leu Asn Gln Glu Glu Lys Arg Arg Asn Ala Asp Ile
1               5                   10                  15

Leu Asn Glu Lys Ile Arg Glu
            20

<210> SEQ ID NO 103
<211> LENGTH: 23
<212> TYPE: PRT
<213> ORGANISM: Homo sapiens

<400> SEQUENCE: 103

Ala Glu Asn Thr Met Leu Thr Ser Lys Leu Lys Glu Lys Gln Asp Lys
1               5                   10                  15

Glu Ile Leu Glu Ala Glu Ile
            20

<210> SEQ ID NO 104
<211> LENGTH: 23
<212> TYPE: PRT
<213> ORGANISM: Homo sapiens

<400> SEQUENCE: 104

Asn Tyr Asn Asn His Leu Lys Asn Arg Ile Tyr Gln Tyr Glu Lys Glu
1               5                   10                  15

Lys Ala Glu Thr Glu Asn Ser
            20

<210> SEQ ID NO 105
<211> LENGTH: 16
<212> TYPE: PRT
<213> ORGANISM: Homo sapiens

<400> SEQUENCE: 105

Ser Arg Arg His His Cys Arg Ser Lys Ala Lys Arg Ser Arg His His
1               5                   10                  15
```